US008372380B2

(12) United States Patent
Barrio et al.

(10) Patent No.: US 8,372,380 B2
(45) Date of Patent: Feb. 12, 2013

(54) IN VIVO IMAGING OF SULFOTRANSFERASES

(75) Inventors: Jorge R. Barrio, Agoura Hills, CA (US); Vladimir Kepe, Los Angeles, CA (US); Gary W. Small, Los Angeles, CA (US); Nagichettiar Satyamurthy, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 283 days.

(21) Appl. No.: 12/594,197

(22) PCT Filed: Mar. 31, 2008

(86) PCT No.: PCT/US2008/004205
§ 371 (c)(1),
(2), (4) Date: Sep. 30, 2009

(87) PCT Pub. No.: WO2008/121407
PCT Pub. Date: Oct. 9, 2008

(65) Prior Publication Data
US 2010/0135906 A1    Jun. 3, 2010

Related U.S. Application Data

(60) Provisional application No. 60/920,875, filed on Mar. 30, 2007.

(51) Int. Cl.
*A61K 51/00* (2006.01)
*A61M 36/14* (2006.01)

(52) U.S. Cl. ...... 424/1.89; 424/1.65; 568/716; 548/152; 546/152; 546/121; 549/23; 549/396

(58) Field of Classification Search .................. 424/1.89
See application file for complete search history.

(56) References Cited

U.S. PATENT DOCUMENTS

| | | | |
|---|---|---|---|
| 6,229,055 B1 | 5/2001 | Klaubert et al. | |
| 2004/0192598 A1 | 9/2004 | Kragie | |
| 2005/0043523 A1* | 2/2005 | Klunk et al. | 534/11 |
| 2006/0122235 A1 | 6/2006 | Iding et al. | |
| 2006/0172335 A1* | 8/2006 | Lowery et al. | 435/6 |
| 2006/0269474 A1* | 11/2006 | Kung et al. | 424/1.11 |

OTHER PUBLICATIONS

Falany et al. Drug Met. Disp. 2006, 34, 361-368.*
Yasuda et al. Tox. Appl. Pharmacol. 2007, 221, 13-20.*
Chapman et al. PNAS 2003, 100, 910-915.*
Mathis et al. J. Nucl. Med. 2004, 45 (suppl), 114P.*
International Search Report and Written Opinion of PCT/US 08/04205 mailed on Jun. 20, 2008.

* cited by examiner

*Primary Examiner* — Michael G Hartley
*Assistant Examiner* — Sean R Donohue
(74) *Attorney, Agent, or Firm* — Christie, Parker & Hale, LLP

(57) ABSTRACT

Radiolabeled tracers for sulfotransferases (SULTs), their synthesis, and their use are provided. Included are substituted phenols, naphthols, coumarins, and flavones radiolabeled with $^{18}F$, $^{123}I$, $^{124}I$, $^{125}I$, or $^{11}C$. Also provided are in vivo techniques for using these and other tracers as analytical and diagnostic tools to study sulfotransferase distribution and activity, in health and disease, and to evaluate therapeutic interventions.

23 Claims, 7 Drawing Sheets

| No. | E₄ | E₃ | Z | W | E₁ | SULT1A1 Km (µM) | SULT1A1 Vmax (nmol/min/mg) | SULT1A1 Vmax/Km | SULT1E1 Km (µM) | SULT1E1 Vmax (nmol/min/mg) | SULT1E1 Vmax/Km |
|---|---|---|---|---|---|---|---|---|---|---|---|
| 1 | OH | H | CH=CH | CH | H | 0.17±0.02 | 14.63±0.61 | 85.1±11.9 | 5.91±0.43 | 3.39±0.08 | 0.57±0.05 |
| 2 | OH | H | NH | CH | H | 0.23±0.05 | 20.26±1.23 | 86.8±17.4 | B.D.L. | B.D.L. | B.D.L. |
| 3 | OH | H | O | CH | H | 0.18±0.02 | 26.5±1.0 | 148±15 | 90.9±7.6 | 2.72±0.37 | 0.03±0.005 |
| 4 | OH | H | S | CH | H | 0.08±0.02 | 9.78±0.61 | 119±24 | 11.5±2.0 | 2.87±0.13 | 0.25±0.05 |
| 5 | OH | H | S | N | H | 2.08±0.39 | 10.35±0.62 | 4.97±.99 | 61.3±5.0 | 2.3±0.1 | 0.04±0.004 |
| 6 | OH | H | O | N | H | 5.5±0.6 | 13.2±0.5 | 2.4±0.24 | 525±110 | 3.3±0.6 | 0.006±0.002 |
| 7 | OH | H | NH | N | H | 19.3±3.7 | 8.5±0.5 | 0.4±0.08 | B.D.L. | B.D.L. | B.D.L. |
| 8 | OH | H | S | N | CH₃ | 6.2±1.1 | 10.3±2.1 | 1.7±0.51 | 6.96±0.75 | 3.29±0.26 | 0.47±0.06 |
| 9 | H | OH | NH | CH | H | 6.62±.97 | 12.84±0.52 | 1.94±0.29 | B.D.L. | B.D.L. | B.D.L. |
| 10 | H | OH | O | CH | H | 0.62±0.08 | 9.87±0.44 | 15.9±1.6 | 177±37 | 1.79±0.25 | 0.01±0.003 |
| 11 | H | OH | S | CH | H | 0.14±0.02 | 11.15±0.66 | 81.7±16.3 | 38.0±5.2 | 2.91±0.16 | 0.08±0.012 |
| 12 | H | OH | S | N | CH₃ | 5.9±2.4 | 19.3±3.8 | 3.3±1.32 | 15.9±0.7 | 4.7±0.1 | 0.30±0.015 |

Fig. 1

| No. | E$_4$ | E$_3$ | Z | W | E$_1$ | SULT1A3 | | | SULT2A1 | | |
|---|---|---|---|---|---|---|---|---|---|---|---|
| | | | | | | Km (µM) | Vmax (nmol/min/mg) | Vmax/Km | Km (µM) | Vmax (nmol/min/mg) | Vmax/Km |
| 1 | OH | H | CH=CH | CH | H | 150±19 | 4.86±0.25 | 0.03±0.004 | 254±149 | 0.19±0.05 | 0.0007±0.0005 |
| 2 | OH | H | NH | CH | H | 2713±742 | 19.48±4.6 | 0.007±0.003 | B.D.L. | B.D.L. | B.D.L. |
| 3 | OH | H | O | CH | H | 377±42 | 8.88±0.55 | 0.02±0.003 | B.D.L. | B.D.L. | B.D.L. |
| 4 | OH | H | S | CH | H | 157±34 | 9.82±1.1 | 0.06±0.001 | B.D.L. | B.D.L. | B.D.L. |
| 5 | OH | H | S | N | H | 280±68 | 8.09±0.98 | 0.03±0.008 | B.D.L. | B.D.L. | B.D.L. |
| 6 | OH | H | O | N | H | 1066±149 | 11.5±1.2 | 0.01±0.002 | B.D.L. | B.D.L. | B.D.L. |
| 7 | OH | H | NH | N | H | B.D.L. | B.D.L. | B.D.L. | B.D.L. | B.D.L. | B.D.L. |
| 8 | OH | H | S | N | CH$_3$ | B.D.L. | B.D.L. | B.D.L. | B.D.L. | B.D.L. | B.D.L. |
| 9 | H | OH | NH | CH | H | 575±89 | 3.66±0.36 | 0.006±0.001 | B.D.L. | B.D.L. | B.D.L. |
| 10 | H | OH | O | CH | H | 385±38 | 8.34±0.46 | 0.02±0.002 | B.D.L. | B.D.L. | B.D.L. |
| 11 | H | OH | S | CH | H | 251±19 | 6.12±0.23 | 0.02±0.002 | B.D.L. | B.D.L. | B.D.L. |
| 12 | H | OH | S | N | CH$_3$ | 1041±212 | 10.1±1.5 | 0.01±0.003 | B.D.L. | B.D.L. | B.D.L. |

Fig. 2

| No. | E4 | E3 | R | SULT1A | | | SULT1E1 | | |
|---|---|---|---|---|---|---|---|---|---|
| | | | | Km (μM) | Vmax (nmol/min/mg) | Vmax/Km | Km (μM) | Vmax (nmol/min/mg) | Vmax/Km |
| 13 | OH | H | H | 0.045±0.01 | 5.25±0.55 | 117±23 | 0.99±0.03 | 3.18±0.87 | 3.22±0.9 |
| 14 | OH | H | NH-CH₃ | B.D.L. | B.D.L. | B.D.L. | 1.6±0.7 | 2.1±.5 | 1.28±0.63 |
| 15 | OH | H | N(CH₃)₂ | B.D.L. | B.D.L. | B.D.L. | 1.33±0.46 | 1.49±.07 | 1.11±0.38 |
| 16 | OH | H | NH₂ | B.D.L. | B.D.L. | B.D.L. | 1.63±0.38 | 2.78±.09 | 1.70±0.39 |
| 17 | OH | H | -OCH₃ | B.D.L. | B.D.L. | B.D.L. | 0.90±0.11 | 1.97±.08 | 2.19±0.26 |
| 18 | OH | H | -NH-CO-CH₃ | B.D.L. | B.D.L. | B.D.L. | 2.36±0.14 | 2.04±.04 | 0.87±0.05 |
| 19 | OH | H | F | B.D.L. | B.D.L. | B.D.L. | 0.92±0.51 | 4.16±.11 | 4.52±2.49 |
| 20 | OH | H | I | B.D.L. | B.D.L. | B.D.L. | 0.52±0.05 | 2.95±.08 | 5.64±0.56 |
| 21 | OH | H | CN | B.D.L. | B.D.L. | B.D.L. | 0.25±0.02 | 4.33±.12 | 17.1±1.4 |
| 22 | OH | H | -SO₂-CH₃ | B.D.L. | B.D.L. | B.D.L. | 1.32±0.08 | 3.57±.06 | 2.69±0.16 |
| 23 | OH | H | NO₂ | B.D.L. | B.D.L. | B.D.L. | 0.12±0.02 | 3.43±.43 | 29.2±5.8 |
| 24 | H | OH | NH-CH₃ | 0.012±.008 | 3.9±1.2 | 325±228 | 1.31±0.61 | 1.82±.11 | 1.39±0.65 |
| 25 | H | OH | N(CH₃)₂ | 0.04±.02 | 11±4 | 275±171 | 0.39±0.07 | 0.98±.10 | 2.47±0.49 |

Fig. 3

| No. | E4 | E3 | R | SULT1A3 | | | SULT2A1 | | |
|---|---|---|---|---|---|---|---|---|---|
| | | | | Km (µM) | Vmax (nmol/min/mg) | Vmax/Km | Km (µM) | Vmax (nmol/min/mg) | Vmax/Km |
| 13 | OH | H | H | B.D.L. | B.D.L. | B.D.L. | B.D.L. | B.D.L. | B.D.L. |
| 14 | OH | H | NH-CH$_3$ | B.D.L. | B.D.L. | B.D.L. | B.D.L. | B.D.L. | B.D.L. |
| 15 | OH | H | N(CH$_3$)$_2$ | B.D.L. | B.D.L. | B.D.L. | B.D.L. | B.D.L. | B.D.L. |
| 16 | OH | H | NH$_2$ | B.D.L. | B.D.L. | B.D.L. | B.D.L. | B.D.L. | B.D.L. |
| 17 | OH | H | -OCH$_3$ | B.D.L. | B.D.L. | B.D.L. | B.D.L. | B.D.L. | B.D.L. |
| 18 | OH | H | -NH-CO-CH$_3$ | B.D.L. | B.D.L. | B.D.L. | B.D.L. | B.D.L. | B.D.L. |
| 19 | OH | H | F | B.D.L. | B.D.L. | B.D.L. | B.D.L. | B.D.L. | B.D.L. |
| 20 | OH | H | I | B.D.L. | B.D.L. | B.D.L. | B.D.L. | B.D.L. | B.D.L. |
| 21 | OH | H | CN | B.D.L. | B.D.L. | B.D.L. | B.D.L. | B.D.L. | B.D.L. |
| 22 | OH | H | -SO$_2$-CH$_3$ | B.D.L. | B.D.L. | B.D.L. | B.D.L. | B.D.L. | B.D.L. |
| 23 | OH | H | NO$_2$ | B.D.L. | B.D.L. | B.D.L. | B.D.L. | B.D.L. | B.D.L. |
| 24 | H | OH | NH-CH$_3$ | B.D.L. | B.D.L. | B.D.L. | B.D.L. | B.D.L. | B.D.L. |
| 25 | H | OH | N(CH$_3$)$_2$ | B.D.L. | B.D.L. | B.D.L. | B.D.L. | B.D.L. | B.D.L. |

Fig. 4

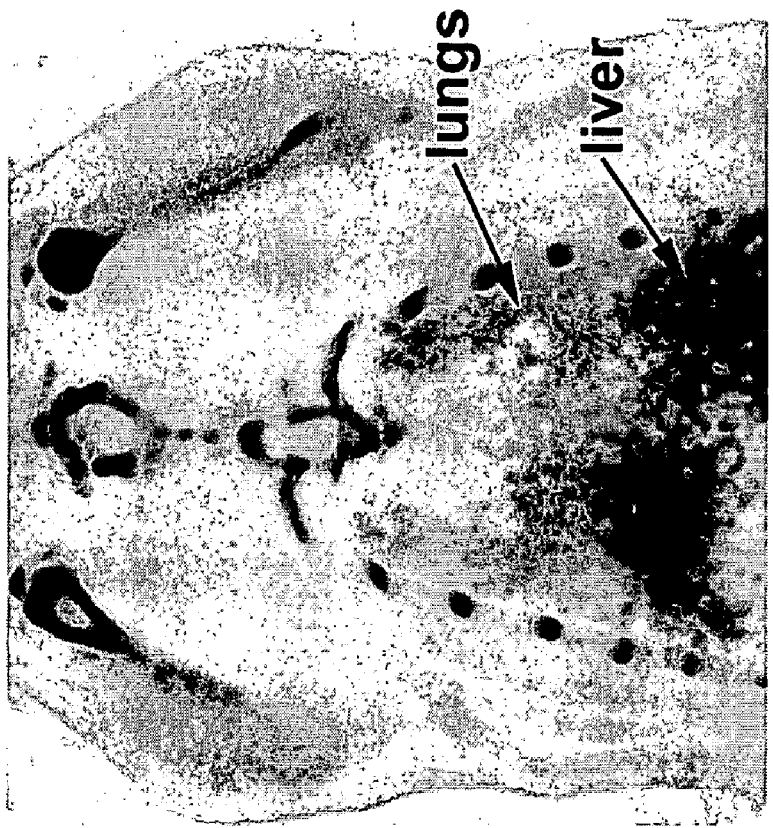
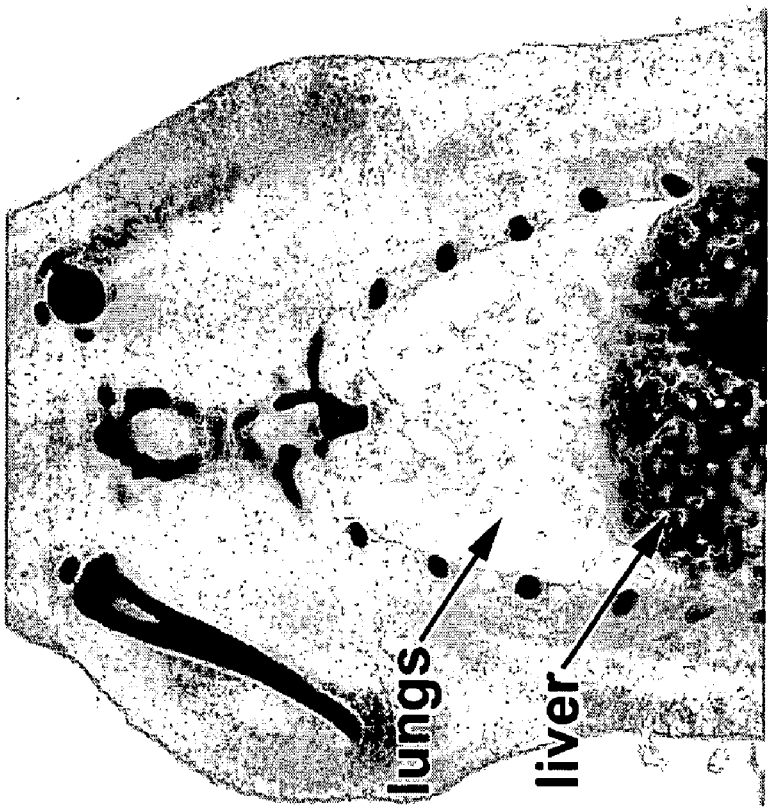
Fig. 5

IN VIVO IMAGING OF SULFOTRANSFERASES

CROSS-REFERENCE—TO RELATED APPLICATION

This application is a National Stage Application under 36 U.S.C. 371(c) of International Application No. PCT/US2008/004205, filed Mar. 31, 2008, which is based on and claims priority of U.S. Provisional Patent Application No. 60/920,875, filed Mar. 30, 2007, the entire contents of both applications being incorporated by reference herein.

ACKNOWLEDGEMENT OF GOVERNMENT SUPPORT

This application was made with government support under Grant No. DE-FC02-02ER63420 (J. R. Barrio), awarded by the United States Department of Energy. The Government has certain rights in the invention.

FIELD OF THE INVENTION

The present invention generally relates to radiolabeled molecular probes (tracers) for monitoring sulfotransferase distribution and activity in vivo.

BACKGROUND OF THE INVENTION

Sulfotransferases ("SULTs") are a class of enzymes that catalyze sulfonation of compounds that carry either a hydroxyl group or an amino group, and play an important role in metabolism of xenobiotics, drugs and many endogenous compounds. They have a wide distribution in the body and act as major metabolic/detoxification systems (Phase II metabolic enzymes) in regulating homeostasis of the body. They are highly expressed in tissues that are exposed to foreign compound: the lungs and respiratory tract (including the nasal cavity), the gastrointestinal tract, and the liver. In the majority of cases, addition of sulfonate moiety to the structure increases its solubility, because sulfates are fully ionized at physiological pH, and decreases biological activity. Yet these enzymes are also capable of bioactivating procarcinogens to reactive electrophiles. (Falany, 1997; Gamage et al., 2006) The universal sulfonate donor for the sulfonations catalyzed by sulfotransferases is 3'-phospho-adenosyl-5'-phosphosulfate (PAPS). (Robbins and Lippman, 1956)

A variety of drugs and natural products are either substrates or inhibitors of these compounds. For example, several natural compounds that exhibit antioxidant and anticancer activity, such as curcumin from curry powder and epigallocatechins from green tea, are potent inhibitors of phenolic sulfotransferases.

The protective role of these sulfotransferase inhibitors may be better understood if we take into account the involvement of sulfotransferases in the activation of several pro-carcinogenic compounds to fully activated carcinogens. This happens when hydroxyl groups in allylic or benzylic alcohols, or in hydroxylamines formed from aromatic amines, get sulfonated. The resulting sulfates are unstable and readily decompose to inorganic sulfate and highly reactive electrophilic carbonium or nitrenium cations. These species can then attack highly nucleophilic DNA and covalently bind to it, which may lead to mutagenesis and carcinogenesis.

Similarly, several drugs or their metabolites having phenolic hydroxyl groups are also metabolized predominantly through sulfonation. Examples include the cancer drugs raloxifene and tamoxifen:

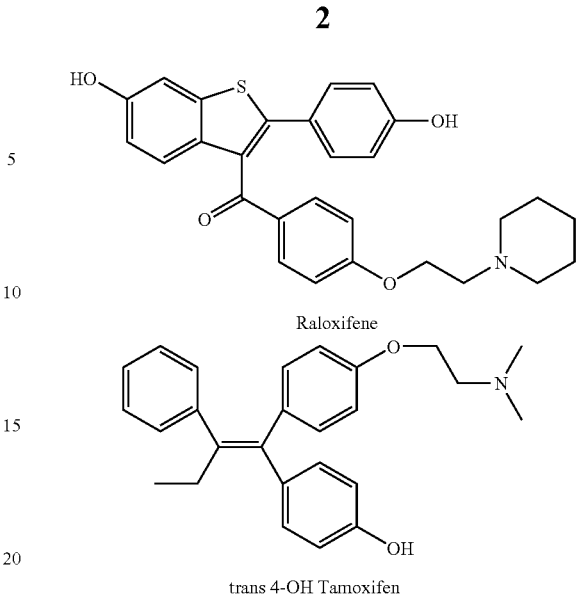

Raloxifene trans 4-OH Tamoxifen

Sulfotransferases can be divided into two large groups: the cytosolic SULTs and the membrane-associated SULTs, which are localized in the Golgi apparatus. Cytosolic SULTs catalyze the sulfonation of xenobiotics, hormones, monoamine neurotransmitters, and drugs. Orally administered xenobiotics and drugs are to a large extent sulfonated in the intestines and in the liver, and excreted either via urine or via bile. Membrane-associated SULTs catalyze the sulfonation of proteins and carbohydrates for processes such as cellular signaling and modulation of receptor binding, such as glycosaminoglycans, glycoproteins, etc. Recent studies have implicated the SULTs in a number of disease states, including entry of the herpes virus, (Xu ea al., 2006) entry of HIV (Seibert et al. 2002), chronic inflammation (van Zante and Rosen, 2003), and cancer (Suzuki et al., 2003).

Five distinctive cytosolic sulfotransferase gene families have been identified in mammals (SULT1-SULT5), of which only SULT1, SULT2 and SULT4 have been identified in humans. (Hempel, 2005) Ten distinctive members of these 3 families were identified: SULT1: A1, A2, A3, B1, C1, C2, E1; SULT2: A1 and B1; and SULT4A1.

SULT1A sulfotransferases are the most abundant and widespread among the 10 members and they differ based on their metabolic preference for different substrates (phenol sulfotransferase SULT1A1, monoamine sulfotransferase SULT1A3).

The major role of sulfonation in the body is metabolism and detoxification of xeno- and endobiotics via conjugation with sulfonate moiety, which makes the compounds more soluble at physiological pH and easier to excrete. In addition to sulfoconjugation of drugs and xenobiotics having hydroxyl groups (or metabolites hydroxylated by Phase I metabolic enzymes), glucuronidation also may contribute in metabolism and excretion of these compounds. Sulfonation and glucuronidation are complementary conjugation processes and take place in different cellular compartments: sulfonation in the cytosol and glucuronidation in the endoplasmic reticulum. Sulfonation is considered a high affinity, low capacity pathway, whereas glucuronidation is considered to be a low affinity, high capacity pathway. (Burchell and Coughtrie, 1997) In general these two enzyme systems also show differences in tissue localization, with major SULT expression occurring in organs facing high exposure to foreign chemicals (e.g., lungs, intestines) and, at the same time, relatively low UDP-glucuronosyltransferase activity in the same organs. (Pacifici et al., 1998)

In addition to metabolism and excretion, sulfonation also plays a strong regulatory role for several classes of endogenous substrates, including estrone, cholesterol, dopamine, bile acid salts, testosterone, and neuroendocrine peptide cholecystokinin (CCK). For example, in normal human plasma, 99% of total dopamine, 78% of total noradrenaline, and 67% of total adrenaline is present in inactive sulfonated form. (Eisenhofer et al., 1999) Similarly, the level of the inactive sulfonated form of the hydroxysteroid hormone dehydroepiandrosterone (DHEA) in plasma is 100-fold higher than the level of unsulfonated DHEA. (Falany, 1997)

Sulfonation can also increase activity of endogenous molecules, as in the case of the neuroendocrine peptide cholecystokinin (CCK), which exhibits biological activity when in sulfated form. (Vargas et al., 1994)

A variety of xenobiotics are substrates for different SULT1 enzymes in the intestines and liver. Examples are (−)-salbutamol, 7-OH-flavone, paracetamol, and (−)-apomorphine. Some natural products and chemicals are potent inhibitors of SULT1A1 and SULT1A3 activities, including 2,6-dichloro-4-nitrophenol (DCNP), curcumin, and quercitin, among others. (Pacifici, 2005)

The human brain displays a moderate level of SULT1 activity. Sulfonation activity for dopamine (SULT1A3) and for p-nitrophenol (SULT1A1) was measured in 17 brain regions of 6 brains from subjects of age 55-74 years. There were considerable regional differences in both SULT activities, with the values for neocortical regions (frontal, parietal, temporal) significantly higher than for the subcortical regions and cerebellum. SULT1A1 activity observed in the frontal cortex was 4.7 times higher than that observed in the thalamus, and SULT1A3 activity was 4.0 times higher in the frontal cortex than in the thalamus. (Young and al., 1984) The authors also assessed the extent of SULT activity loss as a function of post-lobectomy delay in a study on brain tissue from 5 lobectomy patients. Loss of activity was 20% in the post-surgery brain samples 8 hours after tissue removal. SULT E1 has been detected in human brain tissue (Miki, et al., 2002)

The immunohistochemical detection of phenol sulfotransferase-containing neurons in tissue samples from 4 normal brains obtained 6-12 hours after death revealed that the immunostaining was localized to the cytosol of specific neuronal populations in each region analyzed, i.e., the hippocampus, thalamus, striatum, and medulla. (The antibody used was cross-reacting with SULTl1A1 and SULTl1A3.) However, no other areas of cortex (frontal, parietal, or occipital) were analyzed, which prevents us from making any significant correlations with the study of Young et al.

R(−)-apomorphine, a drug used for treatment of Parkinson's disease has been found to be sulfonated by the brain SULT1A enzymes. As in the case of liver and intestinal sulfonation of this drug, it can be blocked with quercitin with IC50 value of 16±2.3 nM. (Vietri et al., 2002b).

In addition to the SULT1 family, the SULT4 family has been discovered and was found to be localized in brain tissues only. (Liyou et al., 2003) Although the authors were unable to identify the substrates for this enzyme, we can conclude, based on very high inter-species preservation of the enzyme structure, that it is involved in an important process.

The Role of Sulfotransferases in Disease

The interaction between sulfotransferases and carcinogens, i.e. activation and inactivation of carcinogens by sulfotransferases, has been extensively studied. (Glatt, 2005). A majority of the pro-carcinogens are aromatic compounds, which can be easily functionalized in such manner that they contain either a benzylic or allylic alcohol or an aromatic hydroxylamine structural unit. The hydroxy group is readily sulfonated by the sulfotransferases, yielding activated sulfuric acid esters of benzylic and allylic alcohols, and aromatic hydroxylamines, which readily lose the sulfate moiety to form resonance-stabilized carbonium or nitrenium ions. These reactive electrophilic species then react with nucleophilic sites on DNA, leading to mutagenicity and carcinogenicity.

The polymorphism of the sulfotransferase SULT1A1 gene leads to Arg-to-His substitution at the codon 213, which leads to lower activity and thermal stability of the enzyme. Several studies have tried to link the decreased activity of SULT1A1 to higher risk for several types of cancers, including gastric cancers among males who drink and smoke (Boccia et al. 2005), head and neck cancer amongst older people who are alcohol and low fruit consumers (Boccia et al., 2006), esophageal cancer in men (Wu et al., 2003), lung cancer in current smokers and current heavy smokers (Wang et al., 2001), and breast cancer (Shatalova et al., 2005).

The SULT1A1 and SULT1A3 sulfotransferases were reported to have increased activity in the thyroid glands of autoimmune thyroid disease patients, and SULT1A1 activity was elevated in nodular goiter patients when compared to healthy controls. (Ebmeier and Anderson, 2004)

Neurodegenerative diseases are another class of diseases with sulfotransferase involvement. A study of SULT1A3 activity performed on brain tissue samples from 7 Parkinson's disease patients and 8 controls suggests that SULT1A3 activity was decreased in all neocortical areas of PD patients (20-39% of controls) when compared with controls, but was increased in the caudate nucleus area with pathology in PD (174-203% of controls). (Baran and Jellinger, 1992)

Although there are no direct reports on the fate of sulfotransferases in Alzheimer's disease (AD), the most common neurodegenerative disease, there is a wealth of evidence that the neuropathological fibrillar deposits found in AD, namely β-amyloid plaques and neurofibrillary tangles, are all associated with heparan sulfate proteoglycans (van Horssen et al., 2003; Verbeek et al., 1999), which may be aiding in fibrillogenesis and also have some anti-protease activity which would protect the amyloid aggregates from degradation the same way as heparan sulfate proteoglycans protect basic fibroblast growth factor from proteolysis when bound to it. (Saksela et al., 1988)

In a way analogous to Parkinson's disease, where the highest SULT1A3 activity is observed in areas having the strongest neurodegeneration in the dopaminergic brain system, we predict that the significant changes of activity and/or expression of SULT1 enzymes in Alzheimer's disease will reflect the global cortical and subcortical distribution of neurodegenerative processes (i.e., neuronal loss, synaptic loss, and formation of neurofibrillary tangles and β-amyloid plaques.

Alzheimer's Disease

Alzheimer's disease is a progressive neurodegenerative disease that affects approximately 20-40% of the population over 80 years of age, the fastest growing age group in the United States and other post-industrial countries. Common features in the brains of patients with Alzheimer's disease include extensive loss of neurons from the vulnerable neuronal population and the presence of neuropathological deposits, including β-amyloid senile plaques (SP) and neurofibrillary tangles (NFT)s. As the disease worsens, the deposits spread throughout the brain in a predictable pattern starting from the medial temporal lobe and progressing gradually to the rest of the cortex. (Braak and Braak, 1991) Related pathologies are seen in other forms of dementia (e.g. Frontotemporal Dementia) and in Down Syndrome.

Since the initial deposits occur much earlier than the symptoms of the disease, early in vivo imaging of these deposits has tremendous diagnostic value. A method using "[$^{18}$F]FDDNP" (2-(1-{6-[(2-[$^{18}$F]fluoroethyl)(methyl)amino]-2-naphthyl}ethylidene)malononitrile), a [F-18]fluorine labeled probe, has been developed for in vivo detection of neuropathological deposits in Alzheimer's disease with positron emission tomography (PET). It has been used to determine in vivo levels of the pathological deposits present in brains of Alzheimer's disease patients, and consistently shows higher levels of [$^{18}$F]FDDNP binding in the brain areas with known pathology when compared with the levels determined in the same areas in the brains of cognitively normal, age-matched subjects (Shoghi-Jadid et al., 2002; Kepe et al., 2004). In vitro results demonstrate the capacity of [$^{18}$F]FDDNP to bind to both major types of neuropathological deposits found in Alzheimer's disease: extracellular β-amyloid senile plaques (SP) and intracellular neurofibrillary tangles (NFT). (Agdeppa et al., 2003a) This binding can be selective blocked by naproxen, a non-steroidal inflammatory drug. (Agdeppa et al., 2003b)

Two other types of [$^{11}$C] carbon-radiolabeled compounds suitable for PET have been developed and are reported to have specific binding to β-amyloid fibrillary aggregates and used for brain PET imaging in Alzheimer's disease. The first is a benzothiazole derivative: 2-[(4'-[$^{11}$C]methylamino)phenyl]-6-hydroxybenzothiazole ("[$^{11}$C]6-OH—BTA-1" or "PIB"), which has been used to study Alzheimer's disease patients and controls with PET (Klunk et al., 2004). The second is a stilbene derivative: 4-([C-11]methylamino)-4'-hydroxystilbene, which has been developed for PET studies and used in a small study with 3 Alzheimer's disease patients and 3 controls. (Verhoef et al., 2004). The results are comparable to the results obtained with [$^{11}$C]6-OH—BTA in the same subjects. As both [C-11]6-OH—BTA and 4-([$^{11}$C]methylamino)-4'-hydroxystilbene are phenolic compounds and therefore sulfotransferase substrates, it is reasonable to assume that at least part of the observed signal results from the sulfonation of both probes in the brain and retention of the resulting sulfates. Indeed, [$^{11}$C]6-OH—BTA has been shown to be sulfonated in the rat brain in vivo. (Mathis et al., 2004)

Although it is recognized that sulfotransferases play an important role in health and disease, no method currently exists for measuring sulfotransferases in vivo, and much remains to be learned about their distribution in the body and their role in the evolution of diseases such as Alzheimer's Disease, cancer, and lung disease related to smoking. An urgent need exists for a method of monitoring the distribution and activity of SULTs in vivo, and for assessing the effect of therapeutic interventions aimed at this class of enzymes.

SUMMARY OF THE INVENTION

It has now been discovered that certain radiolabeled compounds are well-suited for use as molecular imaging probes (sometimes referred to as "radiographic tracers," "radiolabeled tracers," or simply, "tracers") for sulfotransferases in vivo. Included are substituted phenols, naphthols, coumarins and, flavones, radiolabeled with $^{18}$F, $^{123}$I, $^{124}$I, $^{125}$I, or $^{11}$C, as more fully presented in Table 1 below. These compounds comprise a first aspect of the invention. A method of making radiolabeled tracers is also provided. Additional tracers for SULTs are presented in Table 2 and include substituted benzothiazoles and similar fused ring compounds, imidazopyridines, and stilbenes, radiolabeled with $^{18}$F, $^{123}$I, $^{124}$I, $^{125}$I, or $^{11}$C.

In another aspect of the invention, a method of assessing SULT distribution and/or activity in a human or non-human mammal; in vivo, is provided, and comprises administering to the mammal a bolus of at least one tracer listed in Table 1, Table 2, or each of Tables 1 and 2; generating dynamic imaging indicative of tracer uptake in the mammal by scanning the mammal using a radiographic technique; and using the generated radiographic data to assess SULT distribution and/or activity in the mammal. One or more regions of interest, e.g., the brain, lungs, heart, liver, etc.—or even the mammal's entire body—can be scanned and SULT activity therein can be monitored dynamically. This aspect of the invention can also be used to assess the effect of various therapeutic interventions aimed at reducing inflammation and other conditions in which SULTs are implicated; to map SULT expression in vivo; and to monitor the effect of exposure to xenobiotics (e.g. in the lungs and respiratory tract, and in the gastrointestinal tract).

BRIEF DESCRIPTION OF THE DRAWINGS

Various aspects, features, and advantages of the invention will become better understood when considered in conjunction with the following detailed description and by making reference to the appended drawings, wherein:

FIG. 1 is a table listing 12 different unlabeled, fused ring compounds (nos. 1-12) of interest for the invention, showing the effect of ring substituents on sulfotransferase (SULT1A1 and SULT1E1) activity ($K_m$, $V_{max}$, $V_{max}/K_m$);

FIG. 2 is a table listing 12 different unlabeled, fused ring compounds (nos. 1-12) of interest for the invention, showing the effect of ring substituents on sulfotransferase (SULT1A3 and SULT2A1) activity ($K_m$, $V_{max}$, $V_{max}/K_m$);

FIG. 3 is a table listing 13 different unlabeled, fused ring compounds (nos. 13-25) of interest for the invention, showing the effect of ring substituents on sulfotransferase (SULT1A1 and SULT1E1) activity ($K_m$, $V_{max}$, $V_{max}/K_m$);

FIG. 4 is a table listing 13 different unlabeled, fused ring compounds (nos. 13-25) of interest for the invention, showing the effect of ring substituents on sulfotransferase (SULT1A3 and SULT2A1) activity ($K_m$, $V_{max}$, $V_{max}/K_m$);

FIG. 5 is a pair of microPET images of sulfotransferase (SULT1E1) expression in rats, generated in vivo using the radiolabeled substrate 2-(4'-([$^{11}$C]-methylamino)phenyl)-6-hydroxybenzothiazole as a tracer, according to the invention;

DETAILED DESCRIPTION

Figure 6:
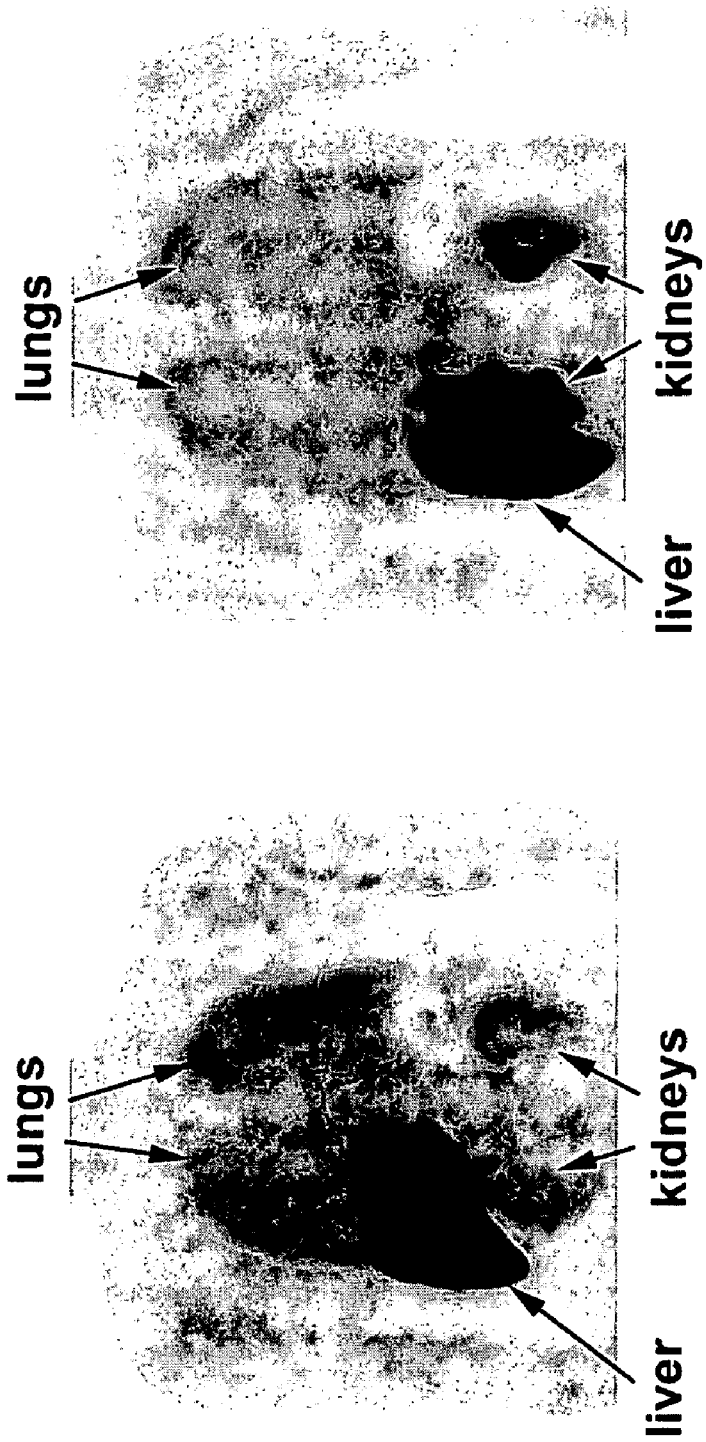
FIG. 6 is a pair of in vivo microPET images of sulfotransferase (SULT1E1) expression in two adult male humans, one a non-smoker and the other a smoker, generated using the radiolabeled substrate 2-(4'-([$^{11}$C]-methylamino)phenyl)-6-hydroxybenzothiazole as a tracer, according to the invention.

The present invention provides radiolabeled tracers that are substrates or inhibitors of sulfotransferases (SULTs), a method of making the tracers, and methods for using the tracers in vivo to assess sulfotransferase distribution and activity in health and disease, as well as the effect of pharmacological agents and xenobiotics that inhibit, promote, or otherwise act on the enzymes when administered to humans and other mammals. In one aspect of the invention, an in vivo method of monitoring one or more SULTs in a mammal is provided. In one embodiment, a bolus of a radiolabeled tracer that functions as a substrate or inhibitor of one or more SULT is administered to a mammal; radiographic data indicative of tracer uptake is generated by scanning the mammal using a radiographic technique, e.g., autoradiography, scintillation counting, PET (including micro-PET), SPECT, etc.; and the generated radiographic data is used to probe or assess SULT distribution or activity in the mammal. In a variation of this embodiment, a dynamic study is performed to establish the time-dependent distribution of the tracer. The invention is used to monitor SULT distribution and function in humans, non-human primates, dogs, rodents, and other mammals, including those having normal SULT genes and those having defective SULT genes. The use of wild type, transgenic, and/or knockout rodents can be particularly useful in certain research programs.

Using this procedure we establish SULT localization based on the functional activity of the radiolabeled substrate used: e.g., If the substrate is specific for SULT1A1. In this sense "activity" can be viewed as the ability of the specific CULT enzyme to transform a radiolabeled substrate into its sulfate resulting in tissue retention. This specific tissue retention is related to the localization and activity of the SULT enzyme and can be measured with radiographic procedures (e.g., PET).

As used herein, the term "radiolabeled" means that the tracer is isotopically enriched with at least one radioisotope. The tracers can be divided into several categories. Table 1 presents substituted phenols, naphthols, coumarins, and flavones, each radiolabeled with $^{18}F$, $^{123}I$, $^{124}I$, $^{125}I$, or $^{11}C$. Table 2 presents substituted benzothiazoles, structurally related fused ring compounds, imidazopyridines, and stilbenes, each radiolabeled with $^{18}F$, $^{123}I$, $^{124}I$, $^{125}I$, or $^{11}C$.

TABLE 1

Selected Radiolabeled Tracers for SULTs

A. PHENOLS (1)

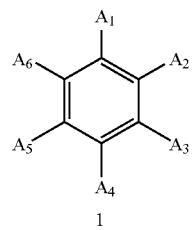

1 where A1 is OH and each of $A_2$-$A_6$ is independently selected from the group of moieties denoted by "K" (defined below), provided that at least one of $A_2$-$A_6$ is or contains a radioisotope; or $A_1$ and $A_3$ are both OH and each of $A_2$, $A_4$-$A_6$ is independently selected from the group of moieties denoted by K, provided that at least one of $A_2$, $A_4$-$A_6$ is or contains a radioisotope.

TABLE 1-continued

Selected Radiolabeled Tracers for SULTs

B. NAPHTHOLS (2)

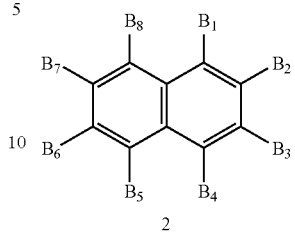

2 where $B_1$ is OH and each of $B_2$-$B_8$ is independently selected from the group of moieties denoted by K, provided that at least one of $B_2$-$B_8$ is or contains a radioisotope; or $B_2$ is OH and each of $B_1$, $B_3$-$B_8$ is independently selected from the group of moieties denoted by K, provided that at least one of $B_1$, $B_3$-$B_8$ is or contains a radioisotope; or $B_1$ and $B_3$ are each OH and each of $B_2$, $B_4$-$B_8$ is independently selected from the group of moieties denoted by K, provided that at least one of $B_4$-$B_8$ is or contains a radioisotope.

C. COUMARINS (3)

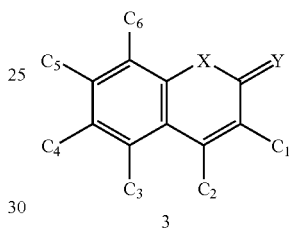

3 where X and Y are, independently, O, S, or N—$R^1$ (wherein $R_1$ is H, alkyl, aryl, [$^{11}C$]methyl, [$^{18}F$]fluoroalkyl, [$^{18}F$]fluoroaryl, [$^{123}I$]iodoalkyl, [$^{123}I$]iodoaryl, [$^{124}I$]iodoalkyl, [$^{124}I$]iodoaryl,] [$^{125}I$]iodoalkyl, or [$^{125}I$]iodoaryl); and wherein
$C_3$ is OH and each of $C_1$-$C_2$, $C_4$-$C_6$ is independently selected from the group of moieties denoted by K; or
$C_4$ is OH and each of $C_1$-$C_3$, $C_5$-$C_6$ is independently selected from the group of moieties denoted by K; or
$C_5$ is OH and each of $C_1$-$C_4$, $C_6$ is independently selected from the group of moieties denoted by K; or
$C_6$ is OH and each of $C_1$-$C_5$ is independently selected from the group of moieties denoted by K; or
$C_2$ and $C_3$ = OH and each of $C_1$, $C_4$-$C_6$ is independently selected from the group of moieties denoted by K; or
$C_2$ and $C_4$ = OH and each of $C_1$, $C_3$, $C_5$-$C_6$ is independently selected from the group of moieties denoted by K; or
$C_2$ and $C_5$ = OH and each of $C_1$, $C_3$-$C_4$, $C_6$ is independently selected from the group of moieties denoted by K; or
$C_2$ and $C_6$ = OH and each of $C_1$, $C_3$-$C_5$ is independently selected from the group of moieties denoted by K; or
$C_3$ and $C_5$ = OH and each of $C_1$-$C_2$, $C_4$, $C_6$ is independently selected from the group of moieties denoted by K; or
$C_4$ and $C_6$ = OH and each of $C_1$-$C_3$, $C_5$ is independently selected from the group of moieties denoted by K; or
$C_2$ = $C_3$ = $C_5$ = OH and each of $C_1$, $C_4$, $C_6$ is independently selected from the group of moieties denoted by K; or
$C_2$, $C_4$ and $C_6$ = OH and each of $C_1$, $C_3$, $C_5$ is independently selected from the group of moieties denoted by K;
and wherein in each case at least one of $C_1$-$C_6$, X, or Y is or contains a radioisotope.

D. FLAVONES (4)

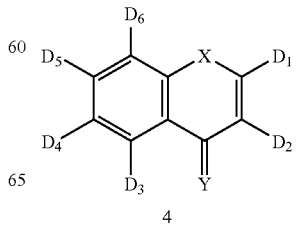

4

TABLE 1-continued

Selected Radiolabeled Tracers for SULTs where X and Y are, independently, O, S, or N—$R^1$ (wherein $R_1$ is H, alkyl, aryl, [$^{11}$C]methyl, [$^{18}$F]fluoroalkyl, [$^{18}$F]fluoroaryl, [$^{123}$I]iodoalkyl, [$^{123}$I]iodoaryl, [$^{124}$I]iodoalkyl, [$^{124}$I]iodoaryl,] [$^{125}$I]iodoalkyl, or [$^{125}$I]iodoaryl); and wherein
$D_3$ is OH and each of $D_1$-$D_2$, $D_4$-$D_6$ is independently selected from the group of moieties denoted by K; or
$D_4$ is OH and each of $D_1$-$D_3$, $D_5$-$D_6$ is independently selected from the group of moieties denoted by K; or
$D_5$ is OH and each of $D_1$-$D_4$, $D_6$ is independently selected from the group of moieties denoted by K; or
$D_6$ is OH and each of $D_1$-$D_5$ is independently selected from the group of moieties denoted by K; or
$D_2$ and $D_3$ = OH and each of $D_1$, $D_4$-$D_6$ is independently selected from the group of moieties denoted by K; or
$D_2$ and $D_4$ = OH and each of $D_1$, $D_3$, $D_5$-$D_6$ is independently selected from the group of moieties denoted by K; or
$D_2$ and $D_5$ = OH and each of $D_1$, $D_3$-$D_4$, $D_6$ is independently selected from the group of moieties denoted by K; or
$D_2$ and $D_6$ = OH and each of $D_1$, $D_3$-$D_5$ is independently selected from the group of moieties denoted by K; or
$D_3$ and $D_5$ = OH and each of $D_1$-$D_2$, $D_4$, $D_6$ is independently selected from the group of moieties denoted by K; or
$D_4$ and $D_6$ = OH and each of $D_1$-$D_3$, $D_5$ is independently selected from the group of moieties denoted by K; or
$D_2$ = $D_3$ = $D_5$ = OH and each of $D_1$, $D_4$, $D_6$ is independently selected from the group of moieties denoted by K; or
$D_2$, $D_4$ and $D_6$ = OH and each of $D_1$, $D_3$, $D_5$ is independently selected from the group of moieties denoted by K;
and wherein in each case at least one of $D_1$-$D_6$, X, or Y is or contains a radioisotope.

TABLE 2

Additional Radiolabeled Tracers for SULTs

E. BENZOTHIAZOLES AND STRUCTURALLY RELATED FUSED RING COMPOUNDS (5)

[Structure 5: fused ring compound with substituents $E_2$, $E_3$, $E_4$, $E_5$, $E_1$, Z, W]

5 where Z is O, S, or N—$R^1$ (wherein $R_1$ is H, alkyl, aryl, [$^{11}$C]methyl, [$^{18}$F]fluoroalkyl, [$^{18}$F]fluoroaryl, [$^{123}$I]iodoalkyl, [$^{123}$I]iodoaryl, [$^{124}$I]iodoalkyl, [$^{124}$I]iodoaryl,] [$^{125}$I]iodoalkyl, or [$^{125}$I]iodoaryl), $CH_2$, or CH=CH; and W is N or CH; and wherein
$E_2$ is OH and each of $E_1$, $E_3$-$E_5$ is independently selected from the group of moieties denoted by K; or
$E_3$ is OH and each of $E_1$-$E_2$, $E_4$-$E_5$ is independently selected from the group of moieties denoted by K; or
$E_4$ is OH and each of $E_1$-$E_3$, $E_5$ is independently selected from the group of moieties denoted by K; or
$E_5$ is OH and each of $E_1$-$E_4$ is independently selected from the group of moieties denoted by K; or
$E_2$ and $E_4$ are OH and each of $E_1$-$E_4$ is independently selected from the group of moieties denoted by K; or
$E_3$ and $E_5$ are OH and each of $E_1$, $E_2$, $E_4$, is independently selected from the group of moieties denoted by K;
and wherein in each case at least one of $E_1$-$E_5$ or Z is or contains a radioisotope.
It is noted that, if Z is S and W is N, the compounds are benzothiazoles; if Z is O and W is N, the compounds are benzooxazoles; and if Z is $CH_2$ and W is N, the compounds are benzoazoles.
A subset of such fused ring compounds, in which $E_1$ is a substituted aryl group, has the formula 5a:

TABLE 2-continued

Additional Radiolabeled Tracers for SULTs

[Structure 5a: fused ring compound with aryl substituent bearing NR'R'' and I']

5a where Z is O, S, N—$R_1$ (wherein $R_1$ is H, alkyl, aryl, [$^{11}$C]methyl, [$^{18}$F]fluoroalkyl, [$^{18}$F]fluoroaryl, [$^{123}$I]iodoalkyl, [$^{123}$I]iodoaryl, [$^{124}$I]iodoalkyl, [$^{124}$I]iodoaryl,] [$^{125}$I]iodoalkyl, or [$^{125}$I]iodoaryl), $CH_2$, or CH=CH; W is N or CH; and I' is H, alkyl, aryl, [$^{11}$C]methyl, $^{18}$F, [$^{18}$F]fluoroalkyl, [$^{18}$F]fluoroaryl, $^{123}$I, [$^{123}$I]iodoalkyl, [$^{123}$I]iodoaryl, $^{124}$I, [$^{124}$I]iodoalkyl, [$^{124}$I]iodoaryl,] $^{125}$I, [$^{125}$I]iodoalkyl, or [$^{125}$I]iodoaryl);
and wherein $E_2$ is OH and each of $E_3$-$E_5$ is independently selected from the group of moieties denoted by K; or
$E_3$ is OH and each of $E_2$, $E_4$-$E_5$ is independently selected from the group of moieties denoted by K; or
$E_4$ is OH and each of $E_2$-$E_3$, $E_5$ is independently selected from the group of moieties denoted by K; or
$E_5$ is OH and each of $E_2$-$E_4$ is independently selected from the group of moieties denoted by K; or
$E_2$ and $E_4$ are OH and each of $E_3$, $E_5$ is independently selected from the group of moieties denoted by K; or
$E_3$ and $E_5$ are OH and each of $E_2$, $E_4$ is independently selected from the group of moieties denoted by K;
wherein in each case at least one of $E_1$-$E_5$, I', or Z is or contains a radioisotope.

F. Structurally related IMIDAZOPYRIDINES (6) having the same combinations of substituents as the fused ring compounds 5 (i.e., $F_1$-$F_5$ are the same as $E_1$-$E_5$), wherein at least one of $F_1$-$F_5$ is or contains a radioisotope.

[Structure 6: imidazopyridine with substituents $F_1$–$F_5$]

6

G. STILBENES (7)

[Structure 7: stilbene with two phenyl rings bearing $G_1$–$G_{10}$ and central $W_1$, $W_2$]

7 where $W_1$ and $W_2$ are, independently, alkyl, aryl, or OH; and wherein
$G_3$ is OH and each of $G_1$-$G_2$, $G_4$-$G_{10}$ is independently selected from the group of moieties denoted by K; or
$G_2$ and $G_4$ are OH and each of $G_1$, $G_3$, $G_5$-$G_{10}$ is independently selected from the group of moieties denoted by K; or
$G_3$ and $G_8$ are OH and each of $G_1$-$G_3$, $G_4$-$G_7$, $G_9$-$G_{10}$ is independently selected from the group of moieties denoted by K; or
$G_2$ = $G_4$ = $G_8$ = OH and each of $G_1$, $G_3$, $G_5$-$G_7$, $G_9$-$G_{10}$ is independently selected from the group of moieties denoted by K;
and wherein in each case at least one of $G_1$-$G_{10}$ is or contains a radioisotope.

Also included are the CIS-STILBENES, in which $W_1$ is cis to $W_2$.

As used herein, "K" denotes the following chemical moieties: H; alkyl; aryl; $^{18}F$; [$^{18}F$]fluoroalkyl; [$^{18}F$]fluoroaryl; $^{123}I$; [$^{123}I$]iodoalkyl; [$^{123}I$]iodoaryl; $^{124}I$; [$^{124}I$]iodoalkyl; [$^{124}I$]iodoaryl; $^{125}I$; [$^{125}I$]iodoalkyl; [$^{125}I$]iodoaryl; —$OR^1$, —$SR^1$, or —$NR^1R^2$ (where $R^1$ and $R^2$ are independently H, alkyl, aryl, [$^{11}C$]methyl, [$^{18}F$]fluoroalkyl; [$^{18}F$]fluoroaryl; [$^{123}I$]iodoalkyl; [$^{123}I$]iodoaryl; [$^{124}I$]iodoalkyl; [$^{124}I$]iodoaryl; [$^{125}I$]iodoalkyl; or [$^{125}I$]iodoaryl); —$NO_2$; —CN; —S(=O)—$R^3$ or —$S(=O)_2$—$R^3$ (where $R^3$ is alkyl, aryl, [$^{11}C$]methyl, [$^{18}F$]fluoroalkyl, [$^{18}F$]fluoroaryl, [$^{123}I$]iodoalkyl, [$^{123}I$]iodoaryl, [$^{124}I$]iodoalkyl, [$^{124}I$]iodoaryl, [$^{125}I$]iodoalkyl, [$^{125}I$]iodoaryl), or —$OR^4$, —$NR^4R^5$, (wherein $R^4$ and $R^5$ are independently H, alkyl, aryl, [$^{11}C$]methyl, [$^{18}F$]fluoroalkyl, [$^{18}F$]fluoroaryl, [$^{123}I$]iodoalkyl, [$^{123}I$]iodoaryl, [$^{124}I$]iodoalkyl, [$^{124}I$]iodoaryl, [$^{125}I$]iodoalkyl, or [$^{125}I$]iodoaryl)); —OC(=O)—$R^6$, —SC(=O)—$R^6$, or —NH—C(=O)—$R^6$ (where $R^6$ is alkyl, aryl, [$^{11}C$]methyl, [$^{18}F$]fluoroalkyl, [$^{18}F$]fluoroaryl, [$^{123}I$]iodoalkyl, [$^{123}I$]iodoaryl, [$^{124}I$]iodoalkyl, [$^{124}I$]iodoaryl, [$^{125}I$]iodoalkyl, [$^{125}I$]iodoaryl).

In one embodiment of the invention, the general protocol for preparing the radiolabeled tracers recited in Tables 1 and 2 includes the following steps: (1) preparation of the radiolabeling agent; (2) reaction with a precursor molecule (radiolabeling); (3) work-up of the reaction mixture; (4) HPLC separation; (5) isolation and identification of the radiolabeled compound; and (6) preparation of the final injectable solution. Radioisotopes are either produced on-site in a cyclotron, in the case of short-lived [$^{11}C$]carbon (half-life 20 min) and [$^{18}F$]fluorine (half-life ~110 min), or obtained from a commercial source (e.g., MDS Nordion, Ottawa, Canada) in the case of the iodine radioisotopes $^{123}I$, $^{124}I$; and $^{125}I$.

The isolation and purification procedures (steps 4 through 6) are common to all radiolabeled compounds. The choice of the HPLC separation conditions (HPLC column and an appropriate solvent or solvent mixtures) is based on chemical properties of the final radiolabeled product and can be determined using standard analytical chemistry techniques. The unlabeled precursor compounds are either purchased or prepared using standard synthetic organic chemistry methods. Sigma-Aldrich provides numerous precursor compounds. A number of benzoxazole compounds, and their syntheses, are described in U.S. Pat. No. 7,045,539; while Int'l Patent Appl., Pub. No. 2007/02400, describes the preparation of benzothiazole fluorinated derivatives and their use as in vivo imaging agents. U.S. Pat. No. 7,250,525 discloses the synthesis of various radiolabeled stilbene derivatives. The synthetic schemes in each of these references are incorporated by reference herein in their entirety. Different radiolabeling agents, synthetic methodologies, reaction conditions, and work-up procedures are employed depending on the structural properties of the unlabeled precursors.

The following types of procedures and agents are representative of those used to prepare the compounds listed in Tables 1 and 2.

Aromatic nucleophilic substitution with non-carrier-added [$^{18}F$]fluoride anion is utilized in the case of polysubstituted phenols having a nitro ($NO_2$) or a halogen leaving group in an ortho or para position to an electron-withdrawing group such as another nitro group or a carbonyl group. The phenolic OH group has to be appropriately protected (e.g. as an alkyl or aryl ether). Examples 1 and 2 below illustrate this for the preparation of 3-[$^{18}F$]fluoro-4-nitrophenol and 4-[$^{18}F$]fluoro-3-nitrophenol, respectively.

Aliphatic nucleophilic substitution with non-carrier-added [$^{18}F$]fluoride anion is used in the case of phenolic compounds having halogen or activated sulfonate ester leaving groups on an alkyl group attached to the benzene ring directly or via a heteroatom (N, O, or S). The phenolic OH group also has to be appropriately protected (e.g. as an alkyl or aryl ether). Typically, an activated sulfonate ester is used. Nonlimiting examples include triflate (trifluoromethanesulfonate), mesylate (methanesulfonate), and tosylate (4-methylbenezenesulfonate).

Alkylation of an amino or hydroxyl group with [$^{11}C$]methyl iodide or triflate, or 2-[$^{18}F$]fluoroalkyl halide or tosylate prepared from non-carrier-added [$^{18}F$]fluoride anion, is used for radiolabeling of the phenolic compounds with a primary amino group, secondary amino group, or an additional phenolic hydroxyl group. The phenolic OH group has to be appropriately protected.

Acylation of an amino or hydroxyl group with an acyl chloride containing [$^{11}C$]carbonyl group. The phenolic OH group has to be appropriately protected.

Electrophilic aromatic substitution of a trialkylstannyl group on a benzene ring of a phenolic compound with carrier-added [$^{18}F$]$F_2$ gas or acetyl hypofluorite. The trialkylstannyl group is introduced via an iodo group on the benzene ring.

Radioiodination proceeds in a similar manner to fluoride synthetic routes.

Nucleophilic Substitutions with [$^{18}F$]fluoride anion. General Procedure.

The choice of solvent and reaction temperature for the nucleophilic substitutions with [$^{18}F$]fluoride anion depends on the chemical stability of the precursor and on the reactivity of the leaving group. In general, nucleophilic aromatic substitution of a nitro group requires heating in more polar solvents at higher temperatures, e.g. dimethyl sulfoxide, whereas the aliphatic nucleophilic substitution of a tosyloxy group on an alkyl chain will already proceed below the boiling point of acetonitrile.

1. Preparation of [$^{18}F$]fluoride salts: cyclotron-produced H[$^{18}F$]F is neutralized with an appropriate base (e.g., cesium carbonate, silver carbonate, potassium carbonate in the presence of potassium chelator Kryptofix 2.2.2, or tri- and tetraammonium salts) and water is removed by distillation, either in vacuo or by co-distillation with anhydrous acetonitrile at elevated temperature (above the boiling point of acetonitrile). An anhydrous polar solvent (e.g., acetonitrile, DMF, various sulfoxides and sulfones) is added to dissolve the [$^{18}F$]fluoride salt for the radiolabeling reaction.

2. An appropriately protected phenolic precursor, dissolved in the same polar solvent as used for dissolving the [$^{18}F$]fluoride salt, is added and the solution allowed to react at elevated temperature (typical range 50° C. to 220° C., depending on the boiling point of the solvent used) for a period of time ranging from 1 min to 30 min.

3. Removal of inorganic salts including unreacted [$^{18}F$] fluoride salt is achieved by dilution of the reaction mixture with water and extraction of organic components from the water solution using a solid phase extraction cartridge.

4. After elution from the solid phase extraction cartridge with a small amount of an organic solvent, the mixture is injected in an appropriate form onto a semi-preparative or preparative high performance liquid chromatography (HPLC) column (either with normal or reverse-phase solid phase) and separated using an appropriate solvent or a solvent mixture.

5. The radiolabeled product is detected using gamma detection, and the HPLC fraction containing the product is collected; the identity of the radiolabeled product is confirmed by co-injection with product carrying the common non-radioactive [F-19]fluorine using an analytical HPLC system.

6. The HPLC solvent is removed either by evaporation in vacuo or, after dilution with water, by extraction with a solid-phase extraction cartridge. The resulting product is dissolved in a small amount of an appropriate solvent, most commonly ethanol, and diluted appropriately to get an injectable solution for human or other biological applications. This solution is sterilized by filtering it through a sterile 0.22 micron filter into a sterile multiinjection vial.

Alkylation with [$^{11}$C]methyl iodide or triflate or with [$^{18}$F] fluoroalkyl halide or tosylate.

1. [$^{11}$C]Methyl iodide is prepared from cyclotron-produced [$^{11}$C]carbon dioxide by LiAlH$_4$ reduction to [$^{11}$C] methanol, followed by iodination with concentrated hydroiodic acid. An alternative route involves [$^{11}$C]carbon dioxide reduction to [$^{11}$C]methane in the gas phase with hydrogen, followed by iodination with I$_2$ at high temperature. Preparation of [$^{11}$C]methyl triflate is achieved by reacting [$^{11}$C]methyl iodide with solid silver triflate.

As an example of a [$^{18}$F]fluorine-containing alkylating agent, 2-[$^{18}$F]fluoro-1-bromoethane can be prepared either from 1,2-dibromoethane or 2-bromoethyl methanesulfonate by aliphatic nucleophilic substitution with non-carrier-added [$^{18}$F]fluoride salts. (See, e.g., Satyamurthy N, Bida G T, Barrio J R, Luxen A, Mazziota J C, Huang S-C, Phelps M E. No-carrier-added 3-(2'-[18F]fluoroethyl)spiperone, a new dopamine receptor-binding tracer for positron emission tomography. Nucl Med Biol 1986; 13:617-624.)

2. Once the alkylating agent has been radiolabeled, it is used to alkylate an NH or OH group on a precursor compound in an appropriate solvent in the presence of a strong base.

The isolation and purification steps are similar to those described above for a nucleophilic [$^{18}$F]fluorination procedure.

Electrophilic Aromatic Substitution of a trialkylstannyl Group on a benzene Ring of a phenolic Compound with Carrier-Added [$^{18}$F]F$_2$ Gas or acetyl hypofluorite.

The trialkylstannyl group is introduced in a reaction of a precursor having an iodo group on the benzene ring with hexamethylditin in the presence of tetrakis-triphenylphosphine palladium (0) in an appropriate solvent (see, e.g., Namavari M, Bishop A, Satyamurthy N, Bida G, Barrio J R. Regioselective radiofluorodestannylation with [$^{18}$F]F$_2$ and [$^{18}$F]CH$_3$COOF: a high yield synthesis of 6-[$^{18}$F]fluoro-L-dopa. Appl Radiat Isot 1992; 43:989-996).

Radioiodination.

Radioiodination of aromatic compounds by a various iodine radioisotopes can be performed using standard oxidative procedure starting from radioactive sodium iodide salt and chloramine-T as an oxidizer.

Once a radiolabeled tracer according to Table 1 and/or Table 2 is prepared, it can be used as described herein as a radiographically detectable substrate for one or more SULTs. Nonlimiting examples of in vivo radiographic techniques include PET (including micro-PET) and SPECT. In a variation of the method, one or more pharmacological or other agents are administered to the animal in vivo, and the effect of the agent(s) is monitored. Optionally, these techniques can be used on lab mammals in combination with autoradiography and/or scintillation counting in tissue acquired post-mortem from the sacrificed lab animals.

For example, in one embodiment of the invention, a radiolabeled tracer as described herein is administered intravenously to a mammal and a dynamic study is performed to establish the time-dependent distribution of the tracer. Because the radiolabeled tracer is a substrate or inhibitor of at least one sulfotransferase, it accumulates in one or more organs, regions of an organ, or other tissues to an extent that is proportional to the amount of SULTs present there.

A particularly beneficial use of the invention is the administration of one or more SULT tracers capable of penetrating the blood-brain barrier to monitor SULT distribution and activity in the healthy, diseased, or injured brain of a human or other mammal. In one embodiment, a bolus of one or more radiolabeled tracers as listed in Table 1 and/or Table 2, selected for its ability to cross the blood-brain barrier, is administered to a human or other mammal, and radiographic data indicative of tracer uptake in the subject's brain is generated by scanning the brain using a radiographic technique, (e.g., PET (including micro PET), SPECT, etc.). The generated radiographic data can be used to probe or assess SULT distribution or activity in the subject's brain. Post-mortem techniques can also be used.

It will be appreciated that a number of variations are included within this aspect of the invention. For example, in one embodiment, the therapeutic effect of a pharmacological or other agent on a sulfotransferase in a mammal is evaluated by (i) administering to a mammal a single bolus or multiple boluses of one or more radiolabeled tracers, e.g., a tracer recited in Table 1 and/or Table 2; (ii) generating a first set of radiographic data by scanning the mammal using a radiographic technique; (iii) administering to the mammal a single bolus or multiple boluses of an actual or putative therapeutic agent; (iv) administering to a mammal a single bolus or multiple boluses of a radiolabeled tracer, e.g., a tracer recited in Table 1 and/or Table 2; (v) generating a second set of radiographic data by scanning the mammal using a radiographic technique; and (vi) comparing the first and second sets of radiographic data. In another embodiment, the method comprises (i) administering to a mammal a bolus of an actual or putative therapeutic agent; (ii) administering to the mammal a bolus of a radiolabeled tracer, e.g., a tracer as recited in Table 1 and/or Table 2; (iii) generating a set of radiographic data by scanning the mammal using a radiographic technique; and (iv) comparing the radiographic data to data obtained in the absence of the agent—i.e., data previously (or subsequently) obtained from the same mammal or from a different mammal.

Advantageously, the radiographic technique can include, or be used in conjunction with, a computerized tomographic (CT) technique or magnetic resonance imaging (MRI) to scan or rescan all or part of the mammal's body, thereby providing an anatomical determination of the test animal and, hence, quantitation of tracer uptake into tissues and organs, both in the presence and in the absence of one or more pharmacological or other agents. Whole body, dynamic body, dynamic brain, and dynamic pelvic/abdominal scans can be carried out. Whole body micro PET in rodents can be employed to monitor SULT activity.

Optionally, additional information can be obtained by also administering one or more pharmacological or other agents to the animal, and monitoring the effect of the agent(s) on tracer uptake and distribution. Nonlimiting examples of suitable agents, include curcuminoids and cancer chemotherapy drugs. Any therapeutic agent can also be used to evaluate its potential role or effect on in vivo activity on SULTs in various organs, or other tissue using in vivo competitive kinetics with the radiolabeled tracer.

In another aspect of the invention, the effect of environmental xenobiotics, such as cigarette smoke, food, pollen, other allergens, irritants, polyaromatic hydrocarbons (PAHs), polychlorinated biphenyls (PCBs), and other known or suspected carcinogens, etc., on SULT distribution and activity is monitored in a way analogous to that described herein for actual and putative therapeutic compounds.

In another aspect of the invention, a tracer that has high affinity for a first SULT, but no or only low affinity for other SULTs, is utilized, allowing one to map or probe different metabolic pathways, as well as the effect of external agents on such pathways. By also administering a pharmacological or other agent to the mammal and monitoring its effect on SULT activity, one can better assess the agent's usefulness (and/or its deleterious effect) on the mammal.

Thus, the distribution/activity of any of the tracers listed in Table 1 can be compared to that of any of the tracers from Table 2. Similarly, comparisons can be made for individual tracers within a given family (phenols, naphthols, etc.). Other permutations and variations are also within the scope of the inventions. As a specific example, 2-(4'-([$^{11}$C]-methylamino)phenyl)-6-hydroxybenzothiazole is a good marker of sulfotransferases, most specifically SULT1E1 (estrogen sulfotransferase), but it is not a substrate for SULT1A1. In contrast, fluoronitrophenols are more specific for SULT1A1. Competition and inhibition studies can be conducted by administering 2-(4'-([$^{11}$C]-methylamino)phenyl)-6-hydroxybenzothiazole (e.g.) to a patient, scanning radiographically, optionally administering another pharmacological agent, and comparing the distribution/activity with that for another tracer described herein, e.g., a fluoronitrophenol.

Imaging methods and analytic methods currently practiced for FDG are readily utilized with the tracers described herein to assess SULT distribution and activity. The following references describe PET, micro-PET, and autoradiographic techniques that will be useful in practicing the invention: (1) Phelps M. E. PET Molecular imaging and its biological applications Springer, N.Y. (2004), including Chapter 1. Cherry, S. R. & Dahlborn, M. PET Physics, Instrumentation and Scanners; Chapter 2 Gambhir, S. S. Quantitative Assay Development for PET; Chapter 4. Barrio, J. R. The molecular basis of disease; Chapter 5, Czernin, J. Oncological applications of FDG-PET; and Chapter 7. Silverman D. H. S. & Melega, W. P. Molecular imaging of biological process with PET. (2) Moore T H, et al. Quantitative assessment of longitudinal metabolic changes in after traumatic brain injury in the adult rat using FDG-microPET. J Cereb Blood Flow Metab. 20(10): 1492-501, (2000); and (3) Matsumura A, et al. Assessment of microPET performance in analyzing the rat brain under different types of anesthesia: comparison between quantitative data obtained with microPET and ex vivo autoradiography. Neuroimage 20: 2040-2050 (2003).

The kinetics of tracer uptake is obtained by tracer kinetic modeling (see for example Carson R. E. Tracer Kinetic Modeling, in: Valk P. E. et al. Positron Emission Tomography, Springer, 2003, and Gambhir, S. S. Quantitative Assay Development for PET, in: Phelps M. E. PET Molecular imaging and its biological applications Springer, N.Y., 2004; Bertoldo, A. et. al. (2005) J. Clinical Endocrinology & Metabolism, 90:1752-1759.

Quantitative comparisons of radiolabeled tracer uptake observed with patients and with normal control subjects will provide information about pathologies. For example, in tumors that have increased levels of SULT (e.g. certain breast cancers), the SULT tracers described herein will be used to stage the tumor and to monitor the effectiveness of surgery, chemotherapy, and/or radiation therapy. Oral administration of the tracers will provide information about the functional activity of SULTs in the intestine, i.e., determination of the amount of tracer uptake into the body provides a measure of functional integrity of the intestine in health and disease.

The use of tracers for in vivo monitoring of drug effects on SULTs should allow researchers to evaluate site of action, dose dependency, length of action and other pharmacokinetic and pharmacodynamic parameters of the drug in animals or human subjects. For example, in one embodiment of the invention, a radiolabeled tracer as described herein is administered to a subject, and PET imaging is used to monitor the effects of drugs on the absorption of tracer from the gut, the reabsorption of tracer from the glomerular filtrate and the uptake of tracer into organs, tissues and tumors. The imaging studies can be carried out before, during and after drug administration.

The invention provides a number of benefits, including use as a diagnostic tool for the detection of neurodegenerative diseases (e.g., Alzheimer's disease, Parkinson's disease, multiple sclerosis, and stroke); use as a diagnostic tool to evaluate the evolution of disease in patients who smoke or abuse drugs; and use as a tool to monitor the role of therapeutic interventions aimed at reducing inflammation by evaluating SULT expression in vivo.

EXAMPLES

The following are nonlimiting examples of the invention.

A variety of non-radiolabeled, aromatic and heteroaromatic phenolic compounds, including 4'-substituted 2-phenyl-6-hydroxybenzothiazoles and similar fused ring compounds, were screened for their abilities to act as substrates for sulfotransferases at concentrations ranging from 10 nM-25 µM. FIGS. 1-4 present sulfonation assay data for 25 compounds. Table 3 provides sulfonation inhibition assay data for selected compounds of interest.

A. Materials

β-Naphthol (BN, a reference control), para-nitrophenol (PNP), estradiol (E2), dehydroepiandrosterone (DHEA), dopamine, dithiothreitol (DTT), and $MgCl_2$ were purchased from Sigma (St. Louis, Mo.). Cytosolic extract of sf-9 insect cells infected with a baculovirus containing SULT cDNAs (SULT1A1, SULT1A3, SULT1E1, SULT2A1) were also purchased from Sigma. [$^{35}$S]-3'-Phosphoadenosine 5'-Phosphosulfate (PAPS)(1-3 Ci/mmol) was purchased from Perkin Elmer (Waltham, Mass.). Aluminum-backed silica TLC plates were purchased from Whatman.

Unlabeled compounds, nos. 1, 11, and 13 can be purchased from Aldrich (Milwaukee, Wis.); no. 2 from Acros Organics (Morris Plains, N.J.), and no. 9 from TCI American (Portland, Oreg.). Compound nos. 3-8 and 10 can be prepared as described in the following references: no. 3: J. Med Chem. 2004, 47, 4829; no. 4: Journal of the Chemical Society, Perkin Transactions 1: Organic and Bio-Organic Chemistry (1972-1999) (1982), (3), 815-21; no. 5: J. Heterocyclic Chem. 2000, 37, 1655 & Chem. Phar. Bull. 1978, 26, 1443; no. 6: U.S. Pat. No. 6,130,217 (2000); no. 7: Synth. Comm., 29(14), 2435-2445, 1999; Archiv der Pharmazie, 308 (7), 550-7, 1975; and JCS, PT I. (11), 2362-70, 1980; no. 8: WO 2004 108694 A1 2004; and no. 10: J. Med Chem. 2004, 47, 4829. Each of these references is incorporated by reference herein in its entirety.

Unlabeled compounds nos. 13-25 can be prepared according to a general methodology for preparing 4'-substituted 6-hydroxybenzothiazoles, using the following three approaches developed for the synthesis of 4'-alkylamino benzothiazoles described by Mathis and colleagues (2003). Some of these compounds are covered by their U.S. Pat. No. 7,270,800 (incorporated by reference herein in its entirety) and related patents.

(a) Reaction of para-methoxybenzoyl chloride with para-substituted anilines results in formation of amides which are then converted into thioamides and cyclized.

(b) Condensation of appropriately para substituted benzoic acids with 2-amino-5-methoxythiophenol in polyphosphoric acid.

(c) Condensation of appropriately para substituted benzaldehydes and 2-amino-5-methoxythiophenol in boiling dimethyl sulfoxide (DMSO).

The resulting 6-methoxybenzothiazoles are de-methylated with $BBr_3$ to form the final 6-hydroxy compounds. Note: To make radiolabeled analogs of these compounds, radiosynthesis is performed using 2-(4'-aminophenyl)-6-hydroxybenzothiazole (prepared as described by Mathis et al., 2003) and [C-11]methyl triflate (as described in Solbach et al., 2005).

B. Sulfonation Assays

Substrate sulfonation assays were performed using cytosolic sulfotransferases SULT1A1, SULT1A3, SULT1E1, and SULT2A1. Enzyme kinetic parameters were determined by using substrate concentration curves. The sulfonation reaction was carried out using [$^{35}$S]-PAPS as the sulfate donor, and the reaction mixture was analyzed using a thin-layer chromatography (TLC) method described in literature (Falany et al., 2006). Reaction mixtures consisted of 10 μL of substrates, originally dissolved in dimethyl sulfoxide and diluted to 1% with Tris-HCl buffer; 50 mM Tris-HCl buffer, pH 7.4; 0.1% bovine serum albumin; 7.5 mM DTT; and 1 μM [$^{35}$S]-PAPS in the final volume of 50 μL. The final concentration of dimethyl sulfoxide was kept at 0.2%. Reactions with SULT1E1 and SULT2A1 were supplemented with 7 mM $MgCl_2$; reactions with SULT1A3 included 1 mM pargyline. Control reactions were performed under identical conditions without addition of substrates. Sulfonation reactions were carried out at 37° C. for 15 min. Enzymatic activity was terminated by precipitation with 50 μL of ice cold methanol and cooling the mixture at −20° C. Subsequently, 20 μL aliquots of the supernatant were spotted on silica gel TLC plates and were developed in t-butanol:acetic acid:water (8:1:1 by volume). Sulfonated products ($R_f$=0.66±0.05) were well separated from unreacted [$^{35}$S]PAPS, which was retained at the origin. TLC plates were exposed on digital autoradiography plates for 2 hrs and read in with a Fuji BAS-5000 digital autoradiography plate reader. The results were quantitated with the software provided with the scanner. Spots were localized and the silica gel was scraped into liquid scintillation vials. Vials were counted using MP-Ecolite+ LS fluid and a Packard Tricarb 2300TR LSC for 5 min per vial. Reactions were monitored for linearity with time and enzyme concentration to ensure the enzyme was the limiting factor.

Sulfonation equilibrium constants ($K_m$), maximum enzyme velocities ($V_{max}$), and substrate efficay ($V_{max}/K_m$) were experimentally determined for the in vitro enzymatic sulfonation of the hydroxy group in each of the compounds listed in FIGS. 1-4 (Nos. 1-25) with the sulfotransferases SULT1A1, SULT1A3 SULT1E1, and SULT2A1. "B.D.L." denotes "below detection limit. The ratio $V_{max}/K_m$ is a measure of substrate catalytic efficiency, based on the Michaelis-Menten equation, $V=V_{max}[S]/K_m+[S]$, where [S] denotes substrate concentration. The results show that 4'-substituted 2-phenyl-6-hydroxy fused azoles and structurally related compounds are specific SULT1E1 substrates. Their efficacy, established by the $V_{max}/K_m$ ratio, is related to the electronegativity of the substituent at the para-aryl position.

In one embodiment of the invention, the data in FIGS. 1-4 is used to select compounds of interest for in vivo investigation of SULT distribution and/or activity in humans and other mammals. Thus, a compound is selected, radiolabeled using a technique as described above, and then administered to a human or other mammal. SULT distribution/activity is observed using a radiographic imaging technique, as described above.

C. Inhibition Assays.

In vitro inhibition reactions were performed using the standard SULT1A1 substrate, para-nitrophenol (PNP), against various 4'-substituted 2-phenyl-6-hydroxybenzothiazoles shown in Table 3. PNP was dissolved in 50 mM Tris-HCl buffer (pH 7.4), and inhibitors were dissolved in dimethyl sulfoxide and diluted to 1% dimethyl sulfoxide concentration with the Tris-HCl buffer. The reaction was carried out with exactly the same method as in the sulfonation assays, except 10 μL of substrate was substituted with 5 μL of PNP and 5 μL of inhibitor. A standard curve for estimating Michaelis-Menten kinetics with PNP and sulfotransferase SULT1A1 was performed initially followed by additional curves in the presence of increasing concentrations of inhibitor. The final methyl sulfoxide concentration was 0.2%. The results are presented in Table 1, wherein $K_i$ denotes the equilibrium constant for sulfonation inhibition.

TABLE 3

Inhibition of sulfotransferase SULT1A1 sulfonation of 4-nitrophenol by different 4'-substituted 2-phenyl-6-hydroxybenzothiazoles.

| | $R^1$ | $R^2$ | $R^3$ | $K_i$ (nM) |
|---|---|---|---|---|
| 14 | OH | H | —NH—$CH_3$ | 5.1 ± 0.3 |
| 17 | OH | H | —$OCH_3$ | 24 ± 2 |
| 18 | OH | H | —NH—C(=O)—$CH_3$ | 100 ± 20 |
| 19 | OH | H | F | 140 ± 10 |

A small value of $K_i$ denotes greater sulfotransferase inhibition. Notably, the benzothiazoles listed in Table 1, which are specific substrates for SULT1E1 and not substrates for SULT1A1 (or any other tested SULT), are excellent inhibitors of SULT1A1. These compounds can be radiolabeled (with, e.g., $^{11}$C, $^{18}$F, $^{125}$I, etc.) using the synthetic methodologies described above.

Example 1

Synthesis of 4-[$^{18}$F]Fluoro-3-nitrophenol, (1-3)

Precursor Preparation (4-chloro-1-(methoxymethoxy)-3-nitrobenzene, 1-1).

To a solution of 4-chloro-3-nitrophenol (173 mg, 1 mmol) and chloromethyl methyl ether (0.15 mL, 2 mmol) in dichloromethane (1 mL) was added triethylamine (0.3 mL, 2.2 mmol). The light yellow solution was stirred at room temperature for 25 min and then evaporated. The yellow oil was purified by column chromatography (40 g silica gel) with hexane/ethyl acetate (6:4) resulting in 133 mg of 4-chloro-1-(methoxymethoxy)-3-nitrobenzene (1-1) as a yellow oil. It was further purified by semi-preparative HPLC (Alltech Econosil Silica 10μ, 10×250 mm; $CH_2Cl_2$/hexane 7:3, 4 mL/min; λ=254 nm; RT=8.0 min). The HPLC product fraction was washed twice with water, dried with sodium sulfate and evaporated. The slight yellow precursor was further dried with co-evaporated with 2×0.5 mL of acetonitrile and dried under high vacuum for 1 hour.

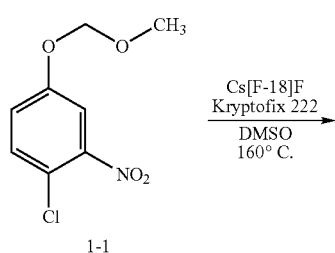

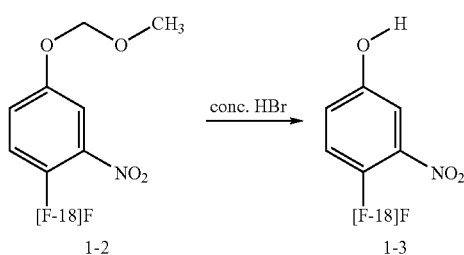

Radiofluorination.

Cyclotron-irradiated [$^{18}$O]-enriched water containing H[$^{18}$F]F was mixed with a solution of 2.1 mg of cesium carbonate in 0.1 mL of water and 0.5 mL of acetonitrile. The volatile components were evaporated under a stream of nitrogen at 115° C. and the residual moisture was co-evaporated with 3×0.5 mL of acetonitrile. The precursor 4-chloro-1-(methoxymethoxy)-3-nitrobenzene (1-1; 6 mg) in 0.5 mL of dimethylsulfoxide was added and the mixture was heated at 160° C. for 10 min.

The reaction mixture was cooled in air for 2 min, then 3 mL of cold 0.1 N hydrochloric acid was added. The resulting mixture was passed through a $C_{18}$ Sep-Pak cartridge, which was previously activated with 5 mL of methanol and washed with 12 mL of water. The Sep-Pak cartridge was washed twice with 6 mL of water and the retained product was eluted with 1.2 mL of methanol. To the methanol solution was added 0.8 mL of 37% HCl and heated at 100° C. for 5 min. The resulting solution was neutralized with 0.8 mL of 11.5 M sodium hydroxide and injected onto a semi-preparative HPLC column (Waters Symmetry Prep $C_{18}$ 7μ, 7.8×300 mm; MeCN/H$_2$O 15:85, 6 mL/min; 254 nm).

The product fraction (RT=35 min) was collected, diluted with the same volume of brine and passed through a $C_{18}$ Sep-Pak cartridge, pre-washed with 5 mL of ethanol and 2×5 mL of water. The Sep-Pak cartridge was washed twice with 5 mL of saline and the radioactive product was eluted with 0.3 mL of ethanol. In this way 15-57 mCi (6-23% radiochemical yield EOS) of the final product was isolated after 2 hour synthesis time.

The radioactive and chemical purities of 4-[$^{18}$F]fluoro-3-nitrophenol (1-3) exceed 95% and were determined on a Waters Symmetry $C_{18}$ analytical HPLC column (5μ, 4.6×150 mm), using tetrahydrofuran, methanol and water mixture (40:20:40) with flow rate at 0.5 mL/min, by radioactivity and UV absorption detection (254 nm). The retention time of 4-[$^{18}$F]fluoro-3-nitrophenol under these conditions is 12 min. The specific radioactivity was determined to be 3,500-5,000 Ci/mmol at the end of synthesis (EOS).

Example 2

Synthesis of 3-[$^{18}$F]fluoro-4-nitrophenol (2-3)

A. Precursor Preparation (3,4-dinitromethoxybenzene, 2-1).

3,4-Dinitrophenol (370 mg, 2 mmol) was dissolved in a mixture of 120 mg of sodium hydroxide (3 mmol) and 5 mL of water. Methyl sulfate (255 mg, 2 mmol) was slowly added and the mixture heated under reflux for 2 hours. The reaction mixture was neutralized by hydrochloric acid and extracted with ethyl acetate. The organic phase was washed with water, dried over magnesium sulfate and evaporated in vacuum. The remaining reddish oil was purified by column chromatography on silica gel using hexane and ethyl acetate as mobile phase. 3,4-Dinitromethoxybenzene (2-1) (198 mg, 72%) was isolated as a reddish solid.

The product was further purified using HPLC (Whatman Partisil silica column, 10 μm, 10×500 mm) with ethyl acetate and hexane as mobile phase.

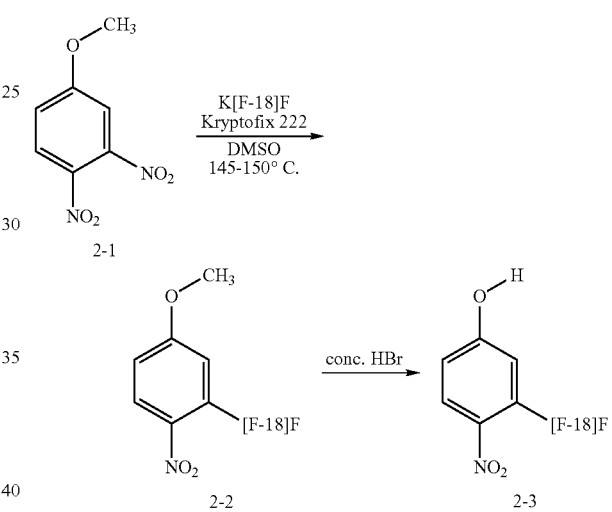

B. Radiolabeling

Cyclotron-irradiated [$^{18}$O]-enriched water containing H[$^{18}$F]F was mixed with a solution of 1 mg of potassium carbonate and 10 mg of Kryptofix 2.2.2 in 0.04 mL of water and 0.96 mL of acetonitrile. Water and acetonitrile were evaporated at 105° C. under a stream of nitrogen and the residual moisture was co-evaporated three times with 0.5 mL of anhydrous acetonitrile. The precursor 3,4-dinitromethoxybenzene (2-1; 5 mg) in 1 mL of anhydrous dimethylsulfoxide was added and the mixture was heated at 145-150° C. for 15 min. After 1 min of cooling in air, 3 mL of water was added and the mixture extracted using a $C_{18}$ SepPak solid phase extraction cartridge, which was activated with 6 mL of ethanol followed by 12 mL of water. The crude mixture was eluted with 1.0 mL of tetrahydrofuran/methanol mixture (1:1), diluted with 1.5 mL of 50 mM sodium phosphate buffer (pH=8.0) and injected onto Waters Symmetry Prep $C_{18}$ semi-preparative HPLC column (7 μm, 7.8×300 mm).

The methoxybenzene 2-2 was eluted with a mixture of tetrahydrofuran, methanol, and sodium phosphate buffer (50 mM, pH=8.0) (25:15:60, respectively) with a flow rate 3 mL/min. 3-[$^{18}$F]fluoro-4-nitromethoxybenzene (2-2) was isolated as a single radioactive peak at ~20 min. The fractions containing methoxybenzene 2-2 were collected, diluted with 5 mL of water and passed through a Waters $C_{18}$ SepPak solid phase extraction cartridge, activated with 5 mL of ethanol followed by 10 mL of water. After extraction, 3-[$^{18}$F]fluoro-4-nitromethoxybenzene was eluted with 6 mL of 10% methanol in ethyl acetate, the eluate collected and evaporated to dryness at 50-60° C. under a stream of nitrogen. 2 mL of 48% hydrobromic acid was added and the mixture heated in a closed vessel at 145-150° C. for 15 min.

After cooling the mixture was neutralized by addition of 1.25 mL of 20% sodium hydroxide, diluted with 2 mL of water and extracted using a $C_{18}$ SepPak solid phase extraction cartridge, which was activated with 6 mL of ethanol followed by 12 mL of water. After an additional 10 mL water wash, the cartridge was eluted with 1 mL of tetrahydrofuran, the eluate mixed with 2 mL of sodium phosphate buffer (50 mM, pH=8.0) and injected onto Waters Symmetry Prep $C_{18}$ semi-preparative HPLC column (7 µm, 7.8×300 mm). The product was eluted as a single peak at ~12 min with a mixture of tetrahydrofuran and sodium phosphate buffer (50 mM, pH=8.0) (20:80, respectively) at 2 mL/min (λ=254 nm).

The product fraction (15-20 mCi) was collected, diluted with the same volume of brine and passed through a $C_{18}$ Sep-Pak cartridge, pre-washed with 5 mL of ethanol and 10 mL of water. The Sep-Pak cartridge was washed twice with 5 mL of saline and the radioactive product was eluted with 0.5 mL of ethanol. In this way 5-10 mCi (2-4% radiochemical yield EOS) of the final product was isolated after 3 hour total synthesis time.

The radioactive and chemical purities of 3-[$^{18}$F]fluoro-4-nitrophenol exceed 95% and were determined on a Waters Symmetry $C_{18}$ analytical HPLC column (5µ, 4.6×150 mm), using tetrahydrofuran and phosphate buffer (50 mM, pH=8.0) (20:80, respectively) with flow rate at 0.5 mL/min, by radioactivity and UV absorption detection (254 nm). The retention time of 3-[$^{18}$F]fluoro-4-nitrophenol under these conditions was 9 min. The specific activity was 2,500-4,000 Ci/mmol at EOS.

Example 3

Use of a Tracer for In Vivo Mapping and Analysis of Function of SULTs in Non-Human Mammals A bolus of a radiolabeled tracer is administered intravenously to a non-human primate, rodent, or other non-human mammal, and the distribution of tracer transport activity is followed by radiographic means, e.g., PET, microPET and/or SPECT. For PET, an intravenous dose of the tracer contains ~0.1-3 mCi/kg (body weight) dissolved in <1 ml of 10% ethanol in saline. The identity of each organ and tissue taking up the tracer can be confirmed by CT scans. Scans can be conducted both with and without administering one or more pharmacological agents, e.g., 2,6-dichloro-4-nitrophenol, quercitin, curcumin, etc.

FIG. 5 depicts in vivo microPET imaging of sulfotransferase SULT1E1 expression in healthy and inflamed lungs in 8-9 month old male Sprague-Dawley rats, using the substrate 2-(4'-([$^{11}$C]-methylamino)phenyl)-6-hydroxybenzothiazole. On the left are shown the chest and upper abdomen of a healthy control rat; on the right is a rat suffering from renal hypertension, chronic progressive nephropathy, and lung inflammation. Both animals were injected with 2.0-2.5 mCi of activity. The images shown were acquired over the period of 15-25 min after injection. Liver metabolizes the tracer rapidly (~90% is in sulfated form after 10-15 min in plasma) and contains a high level of activity. The lungs in the healthy rat are indistinguishable from the background. In contrast, the lungs in the rat with lung inflammation show increased uptake. Warmer colors represent higher levels of tracer uptake.

Metabolite analysis was performed using reverse phase C-18 TLC plates and a mixture of methanol, acetic acid and water (80:5:15, respectively). Plasma was de-proteinated with addition of an equal volume of methanol. The supernatant was spotted on the plates and the plates developed in the mobile phase. The analysis of the plates was performed as described above in the description of the sulfonation assays (Ex. 1-25). Metabolites were identified as follows: 100 mL samples of plasma were mixed with 500-1000 U of either steroid sulfotransferase (to remove the sulfonated metabolite) or glucoronidase (to remove glucoronidated metabolite). The reaction mixtures were incubated at 37° C. for 15 min and the reactions were stopped by addition of 200 mL of ice cold methanol. The supernatants were analyzed as described above and the results compared with the results for un-treated plasma.

Figure 7:
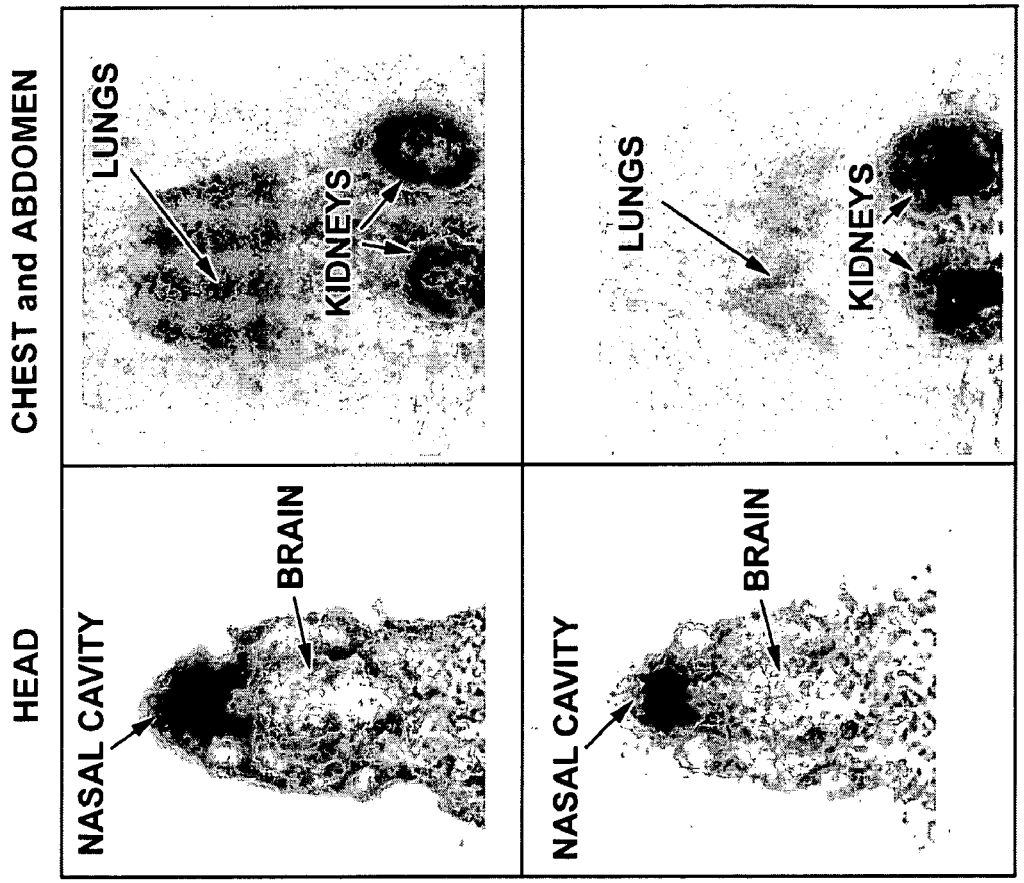
FIG. 7 is a set of four microPET images of sulfotransferase activity and inhibition in a pair of Sprague-Dawley rats, one healthy and one suffering from renal hypertension, chronic progressive nephropathy, and lung inflammation, generated in vivo using the substrate 4-[$^{18}$F]-fluoro-3-nitrophenol as a tracer and 2,6-dichloro-4-nitrophenol as an inhibitor, according to the invention.

FIG. 7 depicts in vivo microPET imaging of sulfotransferase activity and inhibition in a male, Sprague-Dawley rat suffering from renal hypertension, chronic progressive nephropathy, and lung inflammation, using 4-[$^{18}$F]-fluoro-3-nitrophenol as a substrate and 2,6-dichloro-4-nitrophenol as an inhibitor. 4-[$^{18}$F]-fluoro-3-nitrophenol was administered as a bolus injection (0.5 to 2.0 mCi) and the rat brain was scanned dynamically for 60 min. Subsequently, the chest was scanned for 5 min., followed by a 5 min. scan of the abdomen. The microPET images in the top row clearly show that 4-[$^{18}$F]-fluoro-3-nitrophenol is a substrate for the sulfotransferase SULT1A1. (Warmer colors indicate a higher amount PET activity, indicative of tracer uptake and interaction with SULT1A1.) The lower row shows the inhibitory effect on SULT1A1 activity caused by administering a 5 mg/Kg dose of 2,6-dichloro-4-nitrophenol at the time of the 4-[$^{18}$F]-fluoro-3-nitrophenol bolus injection.

Example 4

Use of a Tracer for In Vivo Mapping and Analysis of Function of SULTs in Humans

A bolus of a radiolabeled tracer is administered to a human subject by intravenous injection, and its uptake into a tumor (in the case of cancer), one or more organs of interest, and/or other tissues of the body is followed radiographically. For a 50-70 kg person, 10 mCi of an appropriate tracer from Table 1 or 2 (e.g.) is dissolved in <10 ml 10% ethanol in saline and is injected intravenously, and the distribution of the tracer is followed dynamically with PET for up to 2 hours (multiple whole-body scans at different time intervals or dynamic PET scan of a specific organ). SULT activity in organs and tissues is determined using tracer kinetic modeling from the PET determined tracer uptake data. The anatomical location of tracer uptake in both normal subjects and cancer patients can be determined using CT scans.

FIG. 6 depicts in vivo PET imaging of sulfotransferase SULT1E1 expression in two adult male humans. The left image shows the chest and upper abdomen of a 45 year old smoker, while the right image shows a 69 year old non-smoker. Increased SULT1E1 expression associated with lung inflammation caused by smoking is clearly visible in the lungs of the smoker. Both subjects were scanned with PET 20-45 minutes after being injected with the tracer 2-(4'-([$^{11}$C]-methylamino)phenyl)-6-hydroxybenzothiazole. The smoker received a dose of 10.5 mCi, and the non-smoker received 10.0 mCi. The images were normalized by dividing the signal values with dose injected per kg of body weight. Liver and kidneys, the organs which metabolize and excrete the tracer, show high level of activity. Lungs show increased level of uptake compared with the background (muscles).

Example 5

Use of a Tracer for In Vivo Monitoring of a Therapeutic Intervention

A radiolabeled tracer is administered to a human or other mammal enterally or parenterally, e.g., as an oral dose or intravenous injection, and whole body PET scans are recorded for up to 2 hours. A therapeutic drug (e.g. curcumin or other curcuminoid, chemotherapeutic agents that target tumors, etc.) or drug candidate is also administered to the subject by an appropriate mode of delivery, and its effect on tracer uptake is monitored. The drug or drug candidate is administered at one or more times before and/or after the start of the PET scan. In this manner, the time, dosage, and route of administration and distribution of the drug and its effect on tracer uptake into organs and tissues is precisely determined based on the PET scan and using tracer kinetic modeling.

Example 6

Use of a Tracer for In Vivo Monitoring of the Effect of a Xenobiotic

A radiolabeled tracer is administered to a human or other mammal enterally or parenterally, e.g., as an oral dose or intravenous injection, and whole body PET scans are recorded for up to 2 hours. An environmental xenobiotic, such as cigarette smoke, food, pollen, other allergens, irritants, polyaromatic hydrocarbons (PAHs), polychlorinated biphenyls (PCBs), and other known or suspected carcinogens, etc. is also administered to the subject by an appropriate mode of delivery, and its effect on tracer uptake is monitored. The xenobiotic is administered at one or more times before and/or after the start of the PET scan. In this manner, the time, dosage, and route of administration and distribution of the xenobiotic and its effect on tracer uptake into organs and tissues is precisely determined based on the PET scan and using tracer kinetic modeling.

The invention has been described with reference to various embodiments and examples, but is not limited thereto. Variations may be made without departing from the invention, which is limited only by the appended claims and equivalents thereof.

REFERENCES

The following references are incorporated herein in their entirety:

Agdeppa E D, Kepe V, Liu J, et al. 2-Dialkylamino-6-acylmalononitrile substituted naphthalenes (DDNP Analogs): novel diagnostic and therapeutic tools in Alzheimer's disease. Mol Imaging Biol 2003a; 4:404-417.

Agdeppa E D, Kepe V, Petrič A, et al. In vitro detection of (S)-naproxen and ibuprofen binding to plaques in the Alzheimer's brain using the positron emission tomography molecular imaging probe 2-(1-[6-[(2-[(18)F]fluoroethyl)(methyl)amino]-2-naphthyl]ethylidene)malononitrile. Neuroscience 2003; 117:723-730.

Baran H, Jellinger K. Human brain phenolsulfotransferase. Regional distribution in Parkinson's disease. J Neural Transm [P-D Sect] 1992; 4:267-276.

Boccia S, Persiani R, La Tone G, Rausei S, Arzani D, Gianfagna F, Romano-Spica V, D'Ugo D, Ricciardi G. Sulfotransferase 1A1 polymorphism and gastric cancer risk: a pilot case-control study. Cancer Lett 2005; 229:235-243.

Boccia S, Cadoni G, La Torre G, Arzani D, Volante M, Cattel C, Gianfagna F, Paludetti G, Almadori G, Ricciardi G. A case-control study investigating the role of sulfotransferase 1A1 polymorphism in head and neck cancer. J Cancer Res Clin Oncol 2006; 132:466-472.

Burchell B, Coughtrie M W. Genetic and environmental factors associated with variation of human xenobiotic glucuronidation and sulfation. Environ Health Perspect 1997; 105: 739-747.

Ebmeier C C, Anderson R J. Human Thyroid Phenol Sulfotransferase Enzymes 1A1 and 1A3: Activities in Normal and Diseased Thyroid Glands, and Inhibition by Thyroid Hormones and Phytoestrogens. J Clin Endocrin Metabol 2004; 89:5597-5605.

Eisenhofer G, Coughtrie M W, Goldstein D S. Dopamine sulphate: and enigma resolved. Clin Exp Pharmacol Physiol Suppl 1999; 26:S41-S53.

Falany C N. Enzymology of human cytosolic sulfotransferases. FASEB J 1997; 11:206-216.

Falany J L, Pilloff D E, Leyh T S, Falany C N. Sulfation of raloxifene and 4-hydroxytamoxifen by human cytosolic sulfotransferases. Drug Metab Dispos. 2006; 34:361-8.

Gamage N, Barnett A, Hempel N, Duggleby R G, Windmill K F, Martin J L, McManus M E. Human sulfotransferases and their role in chemical metabolism. Toxicol Sci 2006; 90:5-22.

Glatt H, Boeing H, Engelke C E H, Ma L, Kulhow A, Pabel U, Pomplun D, Teubner W, Meinl W. Human cytosolic sulphotransferases: genetics, characteristics, toxicological aspects. Mutat Res 2001; 482; 27-40.

Glatt H. Activation and inactivation of carcinogens and mutagens by human sulfotransferases. In 'Human Cytosolic Sulfotransferases'; Pacifici G M and Coughtrie M W H, Eds. Taylor & Francis; Boca Raton, London, New York, Singapore; 2005, pp. 279-304.

Hempel N, Barnett A, Gamage N, Duggleby R G, Windmill K F, Martin J L, McManus M E. Human SULT1A SULTs. In 'Human Cytosolic Sulfotransferases'; Pacifici G M and Coughtrie M W H, Eds. Taylor & Francis; Boca Raton, London, New York, Singapore; 2005, pp. 179-230.

Kepe V, Shoghi-Jadid K, Wu H-M, et al. Global and regional [F-18]FDDNP binding as in vivo measure of Alzheimer's disease neuropathology. J Nucl Med 2004; 45Suppl: 126P.

Klunk W E, Engler H, Nordberg A, et al. Imaging brain amyloid in Alzheimer's disease with Pittsburgh Compound-B. Ann Neurol 2004; 55:306-319.

Liyou E N, Buller K M, Tresillian M J, Elvin C J, Scott H L, Dodd P R, Tannenberg A E G, McManus M E. Localization of a brain sulfotransferase, SULT4A1, in the human and rat brain: an immunohistochemical study. J Histochem Cytochem 2003; 51:1655-1664.

Mathis C A, Wang Y, Holt D P, Huang G-F, Debnath M L, Klunk W E. Synthesis and Evaluation of 11C-Labeled 6-Substituted 2-Arylbenzothiazoles as Amyloid Imaging Agents. J Med Chem 2003; 46:2740-2754.

Mathis C A, Holt D P, Wang Y. Huang G F, Debnath M L, Shao L. Klunk W E. Species-dependent metabolism of the amyloid imaging agent [C-11]PIB. J Nucl Med 2004; 45Suppl:114P.

Mild Y, Nakata T, Suuki T, Darnel A D, Moriya T, Kaneko C, Hidaka K, Shiotsu Y, Kusaka H, Sasano H, Systemic Distribution of Steroid Sulfatase and Estrogen Sulfotransferace in Human Adult and Fetal Tissue, J. Clin. Endocrin. & Metab. 87(12):5760-5768 (2002).

Pacifici G M, Quilici M C, Giulianetti B, Spisni R, Nervi M, Guilianu L, Gomeni R. Ritodrine sulfation in the human liver and duodenal mucosa: interindividual variability. Eur J Drug Metab Pharmacokin 1998; 23:64-74.

Pacifici G M. Sulfation of drugs. In 'Human Cytosolic Sulfotransferases'; Pacifici G M and Coughtrie M W H, Eds. Taylor & Francis; Boca Raton, London, New York, Singapore; 2005, pp. 157-177.

Robbins P W, Lippman F. Identification of enzymatically active sulfate as adenosine-3'-phosphate-5'-phosphosulfate. J Am Chem Soc 1956; 78:2652-2654.

Saksela O, Moscatelli D, Sommer A, Rifkin D B. Endothelial cell-derived heparan sulfate binds basic fibroblast growth factor and protects it from proteolytic degradation. J Cell Biol 1988; 107:743-751.

Seibert C, Cadene M, Sanfiz A, Chait B T, Sakmar T P. Tyrosine sulfation of CCR5 N-terminal peptide by tyrosylprotein sulfotransferases 1 and 2 follows a discrete pattern and temporal sequence. Proc Natl Acad Sci USA 2002; 99:11031-11036.

Shatalova E G, Walther S E, Favorova O O, Rebbeck T R, Blanchard R L. Genetic polymorphisms in human SULT1A1 and UGT1A1 genes associate with breast tumor characteristics: a case-series study. Breast Cancer Res 2005; 7:R909-R921.

Shoghi-Jadid K, Small G W, Agdeppa E D, et al. Localization of neurofibrillary tangles and beta-amyloid plaques in the brains of living patients with Alzheimer disease. Am J Geriatr Psychiatry 2002; 10:24-35.

Solbach C, Uebele M, Reischl G, H.-J. Machulla H-J. Efficient radiosynthesis of carbon-11 labeled uncharged Thioflavin T derivatives using [11C]methyl triflate for β-amyloid imaging in Alzheimer's Disease with PET. Appl Radiat Isotop 2005; 62:591-595.

Suzuki T, Nakata T, Miki Y, Kaneko C, Moriya T, Ishida T, Akinaga S, Hirakawa H, Kimura M, Sasano H. Estrogen sulfotransferase and steroid sulfatase in human breast carcinoma. Cancer Res 2003; 63:2762-2770.

van Horssen J, Wesseling P, van den Heuvel L P W J, de Waal R M W, Verbeek M M. Heparan sulphate proteoglycans in Alzheimer's disease and amyloid-related disorders. Lancet Neurol 2003; 2: 482-492.

Vargas F, Frerot O, Brion F, Trung Tuong M D, Lafitte A, Gulat-Marnay C. 3'-Phosphoadenosine 5'-phosphosulfate biosynthesis and the sulfation of cholecystokinin by the tyrosylprotein-sulfotransferase in rat brain tissue. Chem Biol Interact 1994; 92:281-291.

Verbeek M M, Otte-Höller I, van den Born J, van den Heuvel L P W J, David G, Wesseling P, de Waal R M W. Agrin Is a Major Heparan Sulfate Proteoglycan Accumulating in Alzheimer's Disease Brain. Am J Pathol, 1999; 155:2115-2125.

Verhoeff N P, Wilson A A, Takeshita S, et al. In vivo imaging of Alzheimer disease beta-amyloid with [11C]SB-13 PET. Am J Geriatr Psychiatry 2004; 12:584-595.

Vietri M, Vaglini F, Cantini R, Pacifici G M. Quercitin inhibits the sulfation of R(−)-apomorphine in human brain. Int J Clin Pharmacol Ther 2002; 41:30-35.

Wang Y, Spitz M R, Tsou A M-H, Zhang K, Makan N, Wu X. Sulfotransferase (SULT) 1A1 polymorphism as a predisposition factor for lung cancer: a case-control analysis. Lung Cancer 2002; 35:137-142.

Wu M-T, Wang Y-T, Ho C-K, Wu D-C, Lee Y-C, Hsu H-K, Kao E-L, Lee J-M. SULT1A1 polymorphism and esophageal cancer in males. Int J Cancer 2003; 103:101-104.

Xu D, Tiwari V, Xia G, Clement C, Shukla D, Liu J. Characterization of heparan sulphate 3-O-sulphotransferase isoform 6 and its role in assisting the entry of herpes simplex virus type 1. Biochem J. 2005; 385:451-459.

Young W F, Okazaki H, Laws Jr. E R, Weinshilboum R M. Human brain phenol sulfotransferase: biochemical properties and regional localization. J Neurochem 1984; 43:706-715.

Van Zante A, Rosen S D. Sulphated endothelial ligands for L-selectin in lymphocyte homing and inflammation. Biochem Soc Trans 2003; 31:313-317.

Von der Kammer H, Pohlner J. Diagnostic and therapeutic use of a sulfotransferase for neurodegenerative diseases. WO 2005/030947.

We acknowledge the assistance of Dr Gyochang Keum for synthesizing many of the compounds presented in this patent application, and Graham Cole (graduate student, Biomedical Physics Program, UCLA) for performing the in vitro enzymatic determinations with sulfotransferases shown in this application.

What is claimed is:

1. A method of assessing sulfotransferase (SULT) distribution or activity in a mammal, in vivo, comprising:
   administering to the mammal a bolus of a radiolabeled tracer;
   generating radiographic data indicative of tracer uptake in the mammal by scanning the mammal using a radiographic technique; and
   using the radiographic data to assess SULT distribution or activity in the mammal;
   wherein the radiolabeled tracer comprises at least one compound selected from the group consisting of
   (a) phenols having the formula (1)

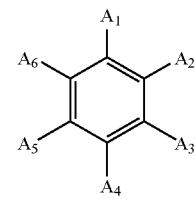

where $A_1$ is OH and each of $A_2$-$A_6$ is independently selected from the group of moieties denoted by "K" (defined below), provided that at least one of $A_2$-$A_6$ is or contains a radioisotope; or $A_1$ and $A_3$ are both OH and each of $A_2$, $A_4$-$A_6$ is independently selected from the group of moieties denoted by K, provided that at least one of $A_2$, $A_4$-$A_6$ is or contains a radioisotope;

(b) naphthols having the formula (2)

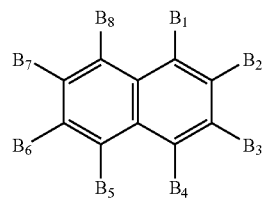

where $B_1$ is OH and each of $B_2$-$B_8$ is independently selected from the group of moieties denoted by K, provided that at least one of $B_2$-$B_8$ is or contains a radioisotope; or $B_2$ is OH and each of $B_1$, $B_3$-$B_8$ is independently selected from the group of moieties denoted by K, provided that at least one of $B_1$, $B_3$-$B_8$ is or contains a radioisotope; or $B_1$ and $B_3$ are each OH and each of $B_2$, $B_4$-$B_8$ is independently selected from the group of moieties denoted by K, provided that at least one of $B_4$-$B_8$ is or contains a radioisotope;

(c) coumarins having the formula (3)

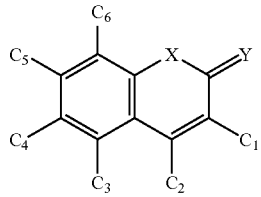

3 where X and Y are, independently, O, S, or N—$R^1$ (wherein $R_1$ is H, alkyl, aryl, [$^{11}$C]methyl, [$^{18}$F]fluoroalkyl, [$^{18}$F]fluoroaryl, [$^{123}$I]iodoalkyl, [$^{123}$I]iodoaryl, [$^{124}$I]iodoalkyl, [$^{124}$I]iodoaryl,] [$^{125}$I]iodoalkyl, or [$^{125}$I]iodoaryl); and wherein
$C_3$ is OH and each of $C_1$-$C_2$, $C_4$-$C_6$ is independently selected from the group of moieties denoted by K; or
$C_4$ is OH and each of $C_1$-$C_3$, $C_5$-$C_6$ is independently selected from the group of moieties denoted by K; or
$C_5$ is OH and each of $C_1$-$C_4$, $C_6$ is independently selected from the group of moieties denoted by K; or
$C_6$ is OH and each of $C_1$-$C_5$ is independently selected from the group of moieties denoted by K; or
$C_2$ and $C_3$=OH and each of $C_1$, $C_4$-$C_6$ is independently selected from the group of moieties denoted by K; or
$C_2$ and $C_4$=OH and each of $C_1$, $C_3$, $C_5$-$C_6$ is independently selected from the group of moieties denoted by K; or
$C_2$ and $C_5$=OH and each of $C_1$, $C_3$-$C_4$, $C_6$ is independently selected from the group of moieties denoted by K; or
$C_2$ and $C_6$=OH and each of $C_1$, $C_3$-$C_5$ is independently selected from the group of moieties denoted by K; or
$C_3$ and $C_5$=OH and each of $C_1$-$C_2$, $C_4$, $C_6$ is independently selected from the group of moieties denoted by K; or
$C_4$ and $C_6$=OH and each of $C_1$-$C_3$, $C_5$ is independently selected from the group of moieties denoted by K; or
$C_2$=$C_3$=$C_5$=OH and each of $C_1$, $C_4$, $C_6$ is independently selected from the group of moieties denoted by K; or
$C_2$, $C_4$ and $C_6$=OH and each of $C_1$, $C_3$, $C_5$ is independently selected from the group of moieties denoted by K;
wherein in each case at least one of $C_1$-$C_6$, X, or Y is or contains a radioisotope;

(d) flavones having the formula (4)

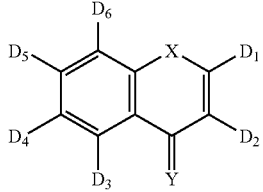

4 where X and Y are, independently, O, S, or N—$R^1$ (wherein $R_1$ is H, alkyl, aryl, [$^{11}$C]methyl, [$^{18}$F]fluoroalkyl, [$^{18}$F]fluoroaryl, [$^{123}$I]iodoalkyl, [$^{123}$I]iodoaryl, [$^{124}$I]iodoalkyl, [$^{124}$I]iodoaryl,] [$^{125}$I]iodoalkyl, or [$^{125}$I]iodoaryl); and wherein
$D_3$ is OH and each of $D_1$-$D_2$, $D_4$-$D_6$ is independently selected from the group of moieties denoted by K; or
$D_4$ is OH and each of $D_1$-$D_3$, $D_5$-$D_6$ is independently selected from the group of moieties denoted by K; or
$D_5$ is OH and each of $D_1$-$D_4$, $D_6$ is independently selected from the group of moieties denoted by K; or
$D_6$ is OH and each of $D_1$-$D_5$ is independently selected from the group of moieties denoted by K; or
$D_2$ and $D_3$ are OH and each of $D_1$, $D_4$-$D_6$ is independently selected from the group of moieties denoted by K; or
$D_2$ and $D_4$ are OH and each of $D_1$, $D_3$, $D_5$-$D_6$ is independently selected from the group of moieties denoted by K; or
$D_2$ and $D_5$ are OH and each of $D_1$, $D_3$-$D_4$, $D_6$ is independently selected from the group of moieties denoted by K; or
$D_2$ and $D_6$ are OH and each of $D_1$, $D_3$-$D_5$ is independently selected from the group of moieties denoted by K; or
$D_3$ and $D_5$ are OH and each of $D_1$-$D_2$, $D_4$, $D_6$ is independently selected from the group of moieties denoted by K; or
$D_4$ and $D_6$ are OH and each of $D_1$-$D_3$, $D_5$ is independently selected from the group of moieties denoted by K; or
$D_2$, $D_3$ and $D_5$ are OH, and $D_1$, $D_4$, $D_6$ is independently selected from the group of moieties denoted by K; or
$D_2$, $D_4$ and $D_6$ are OH, and $D_1$, $D_3$, $D_5$ is independently selected from the group of moieties denoted by K;
wherein in each case at least one of $D_1$-$D_6$, X, or Y is or contains a radioisotope;

(e) fused ring compounds having the formula (5)

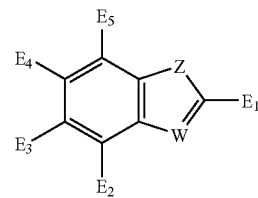

5 where Z is O, S, N—$R^1$ (wherein $R^1$ is H, alkyl, aryl, [$^{11}$C]methyl, [$^{18}$F]fluoroalkyl, [$^{18}$F]fluoroaryl, [$^{123}$I]iodoalkyl, [$^{123}$I]iodoaryl, [$^{124}$I]iodoalkyl, [$^{124}$I]iodoaryl,] [$^{125}$I]iodoalkyl, or [$^{125}$I]iodoaryl), $CH_2$, or CH=CH; and W is N or CH; and wherein
E2 is OH and each of E1, $E_3$-$E_5$ is independently selected from the group of moieties denoted by K; or
$E_3$ is OH and each of E1-E2, $E_4$-$E_5$ is independently selected from the group of moieties denoted by K; or
$E_4$ is OH and each of E1-$E_3$, $E_5$ is independently selected from the group of moieties denoted by K; or
$E_5$ is OH and each of E1-$E_4$ is independently selected from the group of moieties denoted by K; or
E2 and $E_4$ are OH and each of E1-$E_4$ is independently selected from the group of moieties denoted by K; or
$E_3$ and $E_5$ are OH and each of E1, E2, $E_4$, is independently selected from the group of moieties denoted by K;
and wherein in each case at least one of E1-$E_5$ or Z is or contains a radioisotope;

(e') structurally related fused ring compounds in which E1 is a substituted aryl group, said compounds having the formula 5a:

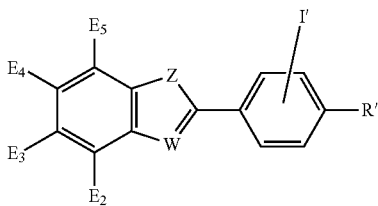

where Z is O, S, N—$R_1$ (wherein $R_1$ is H, alkyl, aryl, [$^{11}$C]methyl, [$^{18}$F]fluoroalkyl, [$^{18}$F]fluoroaryl, [$^{123}$I]iodoalkyl, [$^{123}$I]iodoaryl, [$^{124}$I]iodoalkyl, [$^{124}$I]iodoaryl,] [$^{125}$I]iodoalkyl, or [$^{125}$I]iodoaryl), $CH_2$, or CH=CH; W is N or CH; and P is H, alkyl, aryl, [$^{11}$C]methyl, $^{18}$F, [$^{18}$F]fluoroalkyl, [$^{18}$F]fluoroaryl, $^{123}$I, [$^{123}$I]iodoalkyl, [$^{123}$I]iodoaryl, $^{124}$I, [$^{124}$I]iodoalkyl, [$^{124}$I]iodoaryl,] $^{125}$I, [$^{125}$I]iodoalkyl, or [$^{125}$I]iodoaryl);

and wherein E2 is OH and each of $E_3$-$E_5$ is independently selected from the group of moieties denoted by K; or $E_3$ is OH and each of E2, $E_4$-$E_5$ is independently selected from the group of moieties denoted by K; or $E_4$ is OH and each of E2-$E_3$, $E_5$ is independently selected from the group of moieties denoted by K; or $E_5$ is OH and each of E2-$E_4$ is independently selected from the group of moieties denoted by K; or E2 and $E_4$ are OH and each of $E_3$, $E_5$ is independently selected from the group of moieties denoted by K; or $E_3$ and $E_5$ are OH and each of E2, $E_4$ is independently selected from the group of moieties denoted by K;

wherein in each case at least one of E1-$E_5$, I', or Z is or contains a radioisotope; and wherein R' is selected from the group consisting of H, NH—$CH_3$, N($CH_3$)$_2$ $NH_2$, $OCH_3$, NH—CO—$CH_3$, F, I, CN, $NO_2$, $SO_2$—$CH_3$, and radiolabeled isotopes thereof;

(f) imidazopyridines having the formula (6):

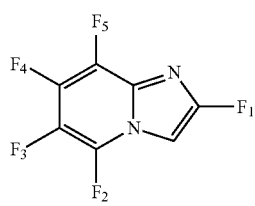

where $F_1$-$F_5$ are the same as E1-$E_5$, and wherein at least one of $F_1$-$F_5$ is or contains a radioisotope; or (g) stilbenes having the formula (7):

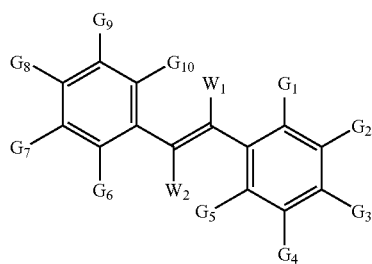

where $W_1$ and $W_2$ are, independently, alkyl, aryl, or OH; and wherein $G_3$ is OH and each of $G_1$-$G_2$, $G_4$-$G_{10}$ is independently selected from the group of moieties denoted by K; or $G_2$ and $G_4$ are OH and each of $G_1$, $G_3$, $G_5$-$G_{10}$ is independently selected from the group of moieties denoted by K; or $G_3$ and $G_8$ are OH and each of $G_1$-$G_3$, $G_4$-$G_7$, $G_9$-$G_{10}$ is independently selected from the group of moieties denoted by K; or $G_2$=$G_4$=$G_8$=OH and each of $G_1$, $G_3$, $G_5$-$G_7$, $G_9$-$G_{10}$ is independently selected from the group of moieties denoted by K; and wherein in each case at least one of $G_1$-$G_{10}$ is or contains a radioisotope;

and wherein, in each of compounds (a)-(g), K is selected from the group consisting of H; alkyl; aryl; $^{18}$F; [$^{18}$F]fluoroalkyl; [$^{18}$F]fluoroaryl; $^{123}$I; [$^{123}$I]iodoalkyl; [$^{123}$I]iodoaryl; $^{124}$I; [$^{124}$I]iodoalkyl; [$^{124}$I]iodoaryl; $^{125}$I; [$^{125}$I]iodoalkyl; [$^{125}$I]iodoaryl; —$SR^1$, or —$NR^1R^2$ (where $R^1$ and $R^2$ are independently H, alkyl, aryl, [$^{11}$C]methyl, [$^{18}$F]fluoroalkyl; [$^{18}$F]fluoroaryl; [$^{123}$I]iodoalkyl; [$^{123}$I]iodoaryl; [$^{124}$I]iodoalkyl; [$^{124}$I]iodoaryl; [$^{125}$I]iodoalkyl; or [$^{125}$I]iodoaryl); —$NO_2$; —CN; —S(=O)—$R^3$ or —S(=O)$_2$—$R^3$ (where $R^3$ is alkyl, aryl, [$^{11}$C]methyl, [$^{18}$F]fluoroalkyl, [$^{18}$F]fluoroaryl, [$^{123}$I]iodoalkyl, [$^{123}$I]iodoaryl, [$^{124}$I]iodoaryl, [$^{125}$I]iodoalkyl, [$^{125}$I]iodoaryl), or —$OR^4$, —$NR^4R^5$, (wherein $R^4$ and $R^5$ are independently H, alkyl, aryl, [$^{11}$C]methyl, [$^{18}$F]fluoroalkyl, [$^{18}$F]fluoroaryl, [$^{123}$I]iodoalkyl, [$^{123}$I]iodoaryl, [$^{124}$I]iodoalkyl, [$^{124}$I]iodoaryl, [$^{125}$I]iodoalkyl, or [$^{125}$I]iodoaryl)); and —OC(=O)—$R^6$, —SC(=O)—$R^6$, or —NH—C(=O)—$R^6$ (where $R^6$ is alkyl, aryl, [$^{11}$C]methyl, [$^{18}$F]fluoroalkyl, [$^{18}$F]fluoroaryl, [$^{123}$I]iodoalkyl, [$^{123}$I]iodoaryl, [$^{124}$I]iodoalkyl, [$^{124}$I]iodoaryl, [$^{125}$I]iodoalkyl, or [$^{125}$I]iodoaryl).

2. A method as recited in claim 1, wherein the mammal is selected from the group consisting of humans, non-human primates, rodents, wild-type rodents, transgenic rodents and knockout rodents, and dogs.

3. A method as recited in claim 1, wherein the radiographic technique comprises positron emission tomography (PET), micro-PET, or single-photon emission computed tomography (SPECT).

4. A method as recited in claim 1, further comprising administering to the mammal at least one actual or putative therapeutic agent, before, during, or after the administration of the radiolabeled tracer.

5. A method as recited in claim 4, wherein the therapeutic agent is administered by injection.

6. A method as recited in claim 1, wherein the radiographic technique comprises one or more computed tomographic scans of all or part of the mammal's body.

7. A method of evaluating therapeutic effect of an agent on a sulfotransferase in a mammal, comprising:

(A) administering a radiolabeled tracer to a mammal; generating a first set of radiographic data by scanning the mammal using a radiographic technique;
administering an actual or putative therapeutic agent to the mammal, intravenously, orally, or by other suitable mode of delivery; generating a second set of radiographic data by scanning the mammal using a radiographic technique; and
comparing the first and second sets of radiographic data; or
(B) administering an actual or putative therapeutic agent to the mammal, intravenously, orally, or by other suitable mode of delivery;
administering a radiolabeled tracer to the mammal;

generating a set of radiographic data by scanning the mammal using a radiographic technique; and
comparing the set of radiographic data to data obtained in the absence of the agent;
wherein in (A) and (B) the radiolabeled tracer comprises at least one compound selected from the group consisting of
(a) phenols having the formula (1)

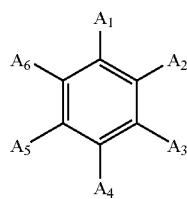

1 where $A_1$ is OH and each of $A_2$-$A_6$ is independently selected from the group of moieties denoted by "K" (defined below), provided that at least one of $A_2$-$A_6$ is or contains a radioisotope; or $A_1$ and $A_3$ are both OH and each of $A_2$, $A_4$-$A_6$ is independently selected from the group of moieties denoted by K, provided that at least one of $A_2$, $A_4$-$A_6$ is or contains a radioisotope;

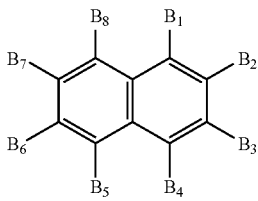

2

(b) naphthols having the formula (2)
where $B_1$ is OH and each of $B_2$-$B_8$ is independently selected from the group of moieties denoted by K, provided that at least one of $B_2$-$B_8$ is or contains a radioisotope; or $B_2$ is OH and each of $B_1$, $B_3$-$B_8$ is independently selected from the group of moieties denoted by K, provided that at least one of $B_1$, $B_3$-$B_8$ is or contains a radioisotope; or $B_1$ and $B_3$ are each OH and each of $B_2$, $B_4$-$B_8$ is independently selected from the group of moieties denoted by K, provided that at least one of $B_4$-$B_8$ is or contains a radioisotope;
(c) coumarins having the formula (3)

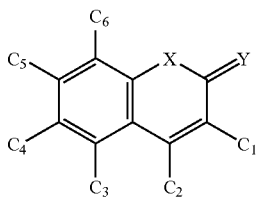

3 where X and Y are, independently, O, S, or N—$R^1$ (wherein $R^1$ is H, alkyl, aryl, [$^{11}$C]methyl, [$^{18}$F]fluoroalkyl, [$^{18}$F]fluoroaryl, [$^{123}$I]iodoalkyl, [$^{123}$I]iodoaryl, [$^{124}$I]iiodoalkyl, [$^{124}$I]iodoaryl,] [$^{125}$I]iodoalkyl, or [$^{125}$I]iodoaryl); and wherein $C_3$ is OH and each of $C_1$-$C_2$, $C_4$-$C_6$ is independently selected from the group of moieties denoted by K; or $C_4$ is OH and each of $C_1$-$C_3$, $C_5$-$C_6$ is independently selected from the group of moieties denoted by K; or
$C_5$ is OH and each of $C_1$-$C_4$, $C_6$ is independently selected from the group of moieties denoted by K; or
$C_6$ is OH and each of $C_1$-$C_5$ is independently selected from the group of moieties denoted by K; or
$C_2$ and $C_3$=OH and each of $C_1$, $C_4$-$C_6$ is independently selected from the group of moieties denoted by K; or
$C_2$ and $C_4$=OH and each of $C_1$, $C_3$, $C_5$-$C_6$ is independently selected from the group of moieties denoted by K; or $C_2$ and $C_5$=OH and each of $C_1$, $C_3$-$C_4$, $C_6$ is independently selected from the group of moieties denoted by K; or
$C_2$ and $C_6$=OH and each of $C_1$, $C_3$-$C_5$ is independently selected from the group of moieties denoted by K; or
$C_3$ and $C_5$=OH and each of $C_1$-$C_2$, $C_4$, $C_6$ is independently selected from the group of moieties denoted by K; or
$C_4$ and $C_6$=OH and each of $C_1$-$C_3$, $C_5$ is independently selected from the group of moieties denoted by K; or
$C_2$=$C_3$=$C_5$=OH and each of $C_1$, $C_4$, $C_6$ is independently selected from the group of moieties denoted by K; or
$C_2$, $C_4$ and $C_6$=OH and each of $C_1$, $C_3$, $C_5$ is independently selected from the group of moieties denoted by K;
wherein in each case at least one of $C_1$-$C_6$, X, or Y is or contains a radioisotope;
(d) flavones having the formula (4)

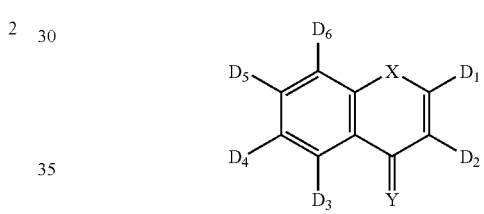

4 where X and Y are, independently, O, S, or N—$R^1$ (wherein R' is H, alkyl, aryl, [$^{11}$C]methyl, [$^{18}$F]fluoroalkyl, [$^{18}$F]fluoroaryl, [$^{123}$I]iodoalkyl, [$^{123}$I]iodoaryl, [$^{124}$I]iodoalkyl, [$^{124}$I]iodoaryl,] [$^{125}$I]iodoalkyl, or [$^{125}$I]iodoaryl); and wherein $D_3$ is OH and each of $D_1$-$D_2$, $D_4$-$D_6$ is independently selected from the group of moieties denoted by K; or
$D_4$ is OH and each of $D_1$-$D_3$, $D_5$-$D_6$ is independently selected from the group of moieties denoted by K; or
$D_5$ is OH and each of $D_1$-$D_4$, $D_6$ is independently selected from the group of moieties denoted by K; or
$D_6$ is OH and each of $D_1$-$D_5$ is independently selected from the group of moieties denoted by K; or
$D_2$ and $D_3$ are OH and each of $D_1$, $D_4$-$D_6$ is independently selected from the group of moieties denoted by K; or
$D_2$ and $D_4$ are OH and each of $D_1$, $D_3$, $D_5$-$D_6$ is independently selected from the group of moieties denoted by K; or $D_2$ and $D_5$ are OH and each of $D_1$, $D_3$-$D_4$, $D_6$ is independently selected from the group of moieties denoted by K; or
$D_2$ and $D_6$ are OH and each of $D_1$, $D_3$-$D_5$ is independently selected from the group of moieties denoted by K; or
$D_3$ and $D_5$ are OH and each of $D_1$-$D_2$, $D_4$, $D_6$ is independently selected from the group of moieties denoted by K; or
$D_4$ and $D_6$ are OH and each of $D_1$-$D_3$, $D_5$ is independently selected from the group of moieties denoted by K; or
$D_2$, $D_3$ and $D_5$ are OH, and $D_1$, $D_4$, $D_6$ is independently selected from the group of moieties denoted by K; or
$D_2$, $D_4$ and $D_6$ are OH, and $D_1$, $D_3$, $D_5$ is independently selected from the group of moieties denoted by K;

(e) fused ring compounds having the formula (5)

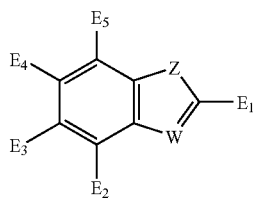

where Z is O, S, N—$R^1$ (wherein $R^1$ is H, alkyl, aryl, [$^{11}$C]methyl, [$^{18}$F]fluoroalkyl, [$^{18}$F]fluoroaryl, [$^{123}$I]iodoalkyl, [23I]iodoaryl, [$^{124}$I]iodoalkyl, [$^{124}$I]iodoaryl,] [$^{125}$I]iodoalkyl, or [$^{125}$I]iodoaryl), $CH_2$, or CH—CH; and W is N or CH; and wherein E2 is OH and each of E1, $E_3$-$E_5$ is independently selected from the group of moieties denoted by K; or $E_3$ is OH and each of E1-E2, $E_4$-$E_5$ is independently selected from the group of moieties denoted by K; or $E_4$ is OH and each of E1-$E_3$, $E_5$ is independently selected from the group of moieties denoted by K; or $E_5$ is OH and each of E1-$E_4$ is independently selected from the group of moieties denoted by K; or E2 and $E_4$ are OH and each of E1-$E_4$ is independently selected from the group of moieties denoted by K; or $E_3$ and $E_5$ are OH and each of E1, E2, $E_4$, is independently selected from the group of moieties denoted by K;

and wherein in each case at least one of E1-$E_5$ or Z is or contains a radioisotope;

(e') structurally related fused ring compounds in which E1 is a substituted aryl group, said compounds having the formula 5a:

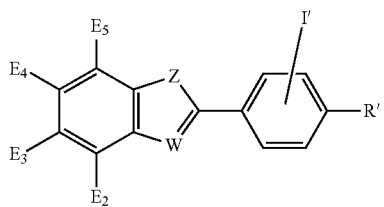

where Z is O, S, N—$R_1$ (wherein $R_1$ is H, alkyl, aryl, [$^{11}$C]methyl, [$^{18}$F]fluoroalkyl, [$^{18}$F]fluoroaryl, [$^{123}$I]iodoalkyl, [$^{123}$I]iodoaryl, [[$^{124}$I]iodoalkyl, [$^{124}$I]iodoaryl,] [$^{125}$I]iodoalkyl, or [$^{125}$I]iodoaryl), $CH_2$, or CH=CH; W is N or CH; and I' is H, alkyl, aryl, [$^{11}$C]methyl, $^{18}$F, [$^{18}$F]fluoroalkyl, [18F]fluoroaryl, 123I, [$^{123}$I]iodoalkyl, [$^{123}$I]iodoaryl, $^{124}$I, [$^{124}$I]iodoalkyl, [$^{124}$I]iodoaryl,] $^{125}$I, [$^{125}$I]iodoalkyl, or [$^{125}$I]iodoaryl);

and wherein E2 is OH and each of $E_3$-$E_5$ is independently selected from the group of moieties denoted by K; or $E_3$ is OH and each of E2, $E_4$-$E_5$ is independently selected from the group of moieties denoted by K; or $E_4$ is OH and each of E2-$E_3$, $E_5$ is independently selected from the group of moieties denoted by K; or $E_5$ is OH and each of $E_4$ is independently selected from the group of moieties denoted by K; or E2 and $E_4$ are OH and each of $E_3$, $E_5$ is independently selected from the group of moieties denoted by K; or $E_3$ and $E_5$ are OH and each of E2, $E_4$ is independently selected from the group of moieties denoted by K;

wherein in each case at least one of E1-$E_5$, I', or Z is or contains a radioisotope; and wherein R' is selected from the group consisting of H, NH—$CH_3$, N($CH_3$)$_2$, $NH_2$, $OCH_3$, NH—CO—$CH_3$, F, I, CN, $NO_2$, $SO_2$—$CH_3$, and radiolabeled isotopes thereof;

(f) imidazopyridines having the formula (6):

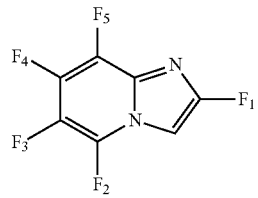

where $F_1$-$F_5$ are the same as E1-$E_5$, and wherein at least one of $F_1$-$F_5$ is or contains a radioisotope; or (g) stilbenes having the formula (7):

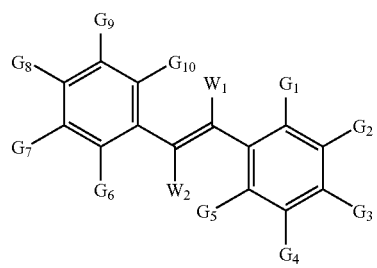

where $W_1$ and $W_2$ are, independently, alkyl, aryl, or OH; and wherein $G_3$ is OH and each of $G_1$-$G_2$, $G_4$-do is independently selected from the group of moieties denoted by K; or $G_2$ and $G_4$ are OH and each of $G_1$, $G_3$, $G_5$-$Gi_0$ is independently selected from the group of moieties denoted by K; or $G_3$ and $G_8$ are OH and each of $G_1$-$G_3$, $G_4$-$G_7$, $G_9$-$G_{10}$ is independently selected from the group of moieties denoted by K; or $G_2$=$G_4$=$G_8$=OH and each of $G_1$, $G_3$, $G_5$-$G_7$, $G_9$-$G_{10}$ is independently selected from the group of moieties denoted by K;

and wherein in each case at least one of $G_1$-$G_{10}$ is or contains a radioisotope;

wherein in each case (a)-(g) K is selected from the group consisting of H; alkyl; aryl; $^{18}$F; [$^{18}$F]fluoroalkyl; [$^{18}$F]fluoroaryl; $^{123}$I; [$^{123}$I]iodoalkyl; [$^{123}$I]iodoaryl; $^{124}$I; [$^{124}$I]iodoalkyl; [$^{124}$I]iodoaryl; $^{125}$I; [$^{125}$I]iodoalkyl; [$^{125}$I]iodoaryl; —$SR^1$, or —$NR^1R^2$ (where $R^1$ and $R^2$ are independently H, alkyl, aryl, [$^{11}$C]methyl, [$^{18}$F]fluoroalkyl; [$^{18}$F]fluoroaryl; [$^{123}$I]iodoalkyl; [$^{123}$I]iodoaryl; [$^{124}$I]iodoalkyl; [$^{124}$I]iodoaryl; $^{125}$I] iodoalkyl; or [$^{125}$I]iodoaryl); —$NO_2$; —CN; —S(=O)—$R^3$ or —S(=O)$_2$—$R^3$ (where $R^3$ is alkyl, aryl, [$^{11}$C]methyl, [$^{18}$F]fluoroalkyl, [$^{18}$F]fluoroaryl, [$^{123}$I]iodoalkyl, [$^{123}$I]iodoaryl, [$^{124}$I]iodoalkyl, [$^{124}$I]iodoaryl, [$^{125}$I]iodoalkyl, [$^{125}$I]iodoaryl), or —$OR^4$, —$NR^4R^5$, (wherein $R^4$ and $R^5$ are independently H, alkyl, aryl, [$^{11}$C]methyl, [$^{18}$F]fluoroalkyl, [$^{18}$F]fluoroaryl, [$^{123}$I]iodoalkyl, [$^{123}$I]iodoaryl, [$^{124}$I]iodoalkyl, [$^{124}$I]iodoaryl, [$^{125}$I]iodoalkyl, or [$^{125}$I]iodoaryl)); and —OC(=O)—$R^6$, —SC(=O)—$R^6$, or —NH—C(=O)—$R^6$ (where $R^6$ is alkyl, aryl, [$^{11}$C]methyl, [$^{18}$F]fluoroalkyl, [$^{18}$F]fluoroaryl, [$^{123}$I]iodoalkyl, [$^{123}$I]iodoaryl, [$^{124}$I]iodoalkyl, [$^{124}$I]iodoaryl, [$^{125}$I]iodoalkyl, or [$^{125}$I]iodoaryl).

8. A method as recited in claim 1, wherein the tracer comprises 4-[$^{18}$F]fluoro-3-nitrophenol.

9. A method as recited in claim 1, wherein the tracer comprises 3-$^{18}$F fluoro-4-nitrophenol.

10. A method as recited in claim 1, further comprising administering to the mammal at least one environmental xenobiotic, before, during, or after administration of the radiolabeled tracer.

11. A method as recited in claim 10, wherein the xenobiotic comprises cigarette smoke or one or more components thereof.

12. A method of monitoring sulfotransferase activity in a mammal's brain, in vivo, comprising: administering to a mammal a bolus of a radiolabeled tracer for a sulfotransferase, which tracer is capable of crossing the mammal's blood-brain barrier; and generating radiographic data indicative of tracer uptake in the mammal's brain by scanning the brain using a radiographic technique, in vivo.

13. A method as recited in claim 12, wherein the mammal's brain is healthy.

14. A method as recited in claim 12, wherein the mammal is suffering from Alzheimer's disease, Parkinson's disease, non-Alzheimer's-type dementia, epilepsy, stroke, brain tumor, multiple sclerosis, or brain injury.

15. A method of monitoring sulfotransferase activity in a mammal, in vivo, comprising:
administering to a mammal a bolus of a first radiolabeled tracer;
generating first radiographic data indicative of first tracer uptake in the mammal by scanning the mammal using a radiographic technique;
administering to the mammal a bolus of a second radiolabeled tracer; generating second radiographic data indicative of second tracer uptake in the mammal by scanning the mammal using a radiographic technique; and
comparing the first radiographic data to the second radiographic data.

16. A method as recited in claim 15, further comprising
using the first radiographic data to assess distribution or activity of a first sulfotransferase in the mammal;
using the second radiographic data to assess distribution or activity of a second sulfotransferase in the mammal; and
comparing the distribution or activity of the first sulfotransferase to that of the second sulfotransferase.

17. A method of monitoring sulfotransferase activity in a mammal, in vivo, comprising:
administering to a mammal a bolus of a first radiolabeled tracer known to be a substrate for a first sulfotransferase, but not a substrate for a second sulfotransferase;
generating first radiographic data indicative of first tracer uptake in the mammal by scanning the mammal using a radiographic technique;
administering to the mammal a bolus of a second radiolabeled tracer; generating second radiographic data indicative of second tracer uptake in the mammal by scanning the mammal using a radiographic technique; and
comparing the first radiographic data to the second radiographic data.

18. A method as recited in claim 16, further comprising
using the first radiographic data to assess distribution or activity of the first sulfotransferase in the mammal;
using the second radiographic data to assess distribution or activity of the second sulfotransferase in the mammal; and
comparing the distribution or activity of the first sulfotransferase to that of the second sulfotransferase.

19. A method as recited in claim 17, wherein the second radiolabeled tracer is known to be a substrate for a second sulfotransferase, but not a substrate for the first sulfotransferase.

20. A method as recited in claim 16, wherein the first radiolabeled tracer comprises a compound selected from the group consisting of
(a) phenols having the formula (1)

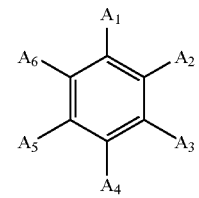

where $A_1$ is OH and each of $A_2$-$A_6$ is independently selected from the group of moieties denoted by "K" (defined below), provided that at least one of $A_2$-$A_6$ is or contains a radioisotope; or $A_1$ and $A_3$ are both OH and each of $A_2$, $A_4$-$A_6$ is independently selected from the group of moieties denoted by K, provided that at least one of $A_2$, $A_4$-$A_6$ is or contains a radioisotope;
(b) naphthols having the formula (2)

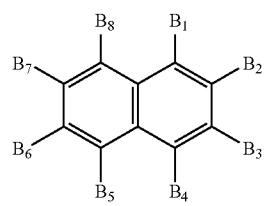

where $B_1$ is OH and each of $B_2$-$B_8$ is independently selected from the group of moieties denoted by K, provided that at least one of $B_2$-$B_8$ is or contains a radioisotope; or $B_2$ is OH and each of $B_1$, $B_3$-$B_8$ is independently selected from the group of moieties denoted by K, provided that at least one of $B_1$, $B_3$-$B_8$ is or contains a radioisotope; or $B_1$ and $B_3$ are each OH and each of $B_2$, $B_4$-$B_8$ is independently selected from the group of moieties denoted by K, provided that at least one of $B_4$-$B_8$ is or contains a radioisotope;
(c) coumarins having the formula (3)

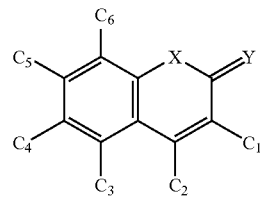

where X and Y are, independently, O, S, or N—$R^1$ (wherein $R^1$ is H, alkyl, aryl, [$^{11}$C]methyl, [$^{18}$F]fluoroalkyl, [$^{18}$F]fluoroaryl, [$^{123}$I]iodoalkyl, [$^{123}$I]iodoaryl, [$^{124}$I]iodoalkyl, [$^{124}$I]iodoaryl,] [$^{125}$I]iodoalkyl, or [$^{125}$I]iodoaryl); and wherein $C_3$ is OH and each of $C_1$-$C_2$, $C_4$-$C_6$ is independently selected from the group of moieties denoted by K; or
$C_4$ is OH and each of $C_1$-$C_3$, $C_5$-$C_6$ is independently selected from the group of moieties denoted by K; or
$C_5$ is OH and each of $C_1$-$C_4$, $C_6$ is independently selected from the group of moieties denoted by K; or
$C_6$ is OH and each of $C_1$-$C_5$ is independently selected from the group of moieties denoted by K; or
$C_2$ and $C_3$=OH and each of $C_1$, $C_4$-$C_6$ is independently selected from the group of moieties denoted by K; or
$C_2$ and $C_4$=OH and each of $C_1$, $C_3$, $C_5$-$C_6$ is independently selected from the group of moieties denoted by K; or $C_2$ and $C_5$=OH and each of $C_1$, $C_3$-$C_4$, $C_6$ is independently selected from the group of moieties denoted by K; or
$C_2$ and $C_6$=OH and each of $C_1$, $C_3$-$C_5$ is independently selected from the group of moieties denoted by K; or
$C_3$ and $C_5$=OH and each of $C_1$-$C_2$, $C_4$, $C_6$ is independently selected from the group of moieties denoted by K; or
$C_4$ and $C_6$=OH and each of $C_1$-$C_3$, $C_5$ is independently selected from the group of moieties denoted by K; or
$C_2$=$C_3$=$C_5$=OH and each of $C_1$, $C_4$, $C_6$ is independently selected from the group of moieties denoted by K; or
$C_2$, $C_4$ and $C_6$=OH and each of $C_1$, $C_3$, $C_5$ is independently selected from the group of moieties denoted by K;
wherein in each case at least one of $C_1$-$C_6$, X, or Y is or contains a radioisotope; and
(d) flavones having the formula (4)

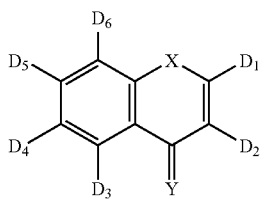

where X and Y are, independently, O, S, or N—$R^1$ (wherein $R^1$ is H, alkyl, aryl, [$^{11}$C]methyl, [$^{18}$F]fluoroalkyl, [$^{18}$F]fluoroaryl, [$^{123}$I]iodoalkyl, [$^{123}$I]iodoaryl, [$^{124}$I]iodoalkyl, [$^{124}$I]iodoaryl,] [$^{125}$I]iodoalkyl, or [$^{125}$I]iodoaryl); and wherein
$D_3$ is OH and each of $D_1$-$D_2$, $D_4$-$D_6$ is independently selected from the group of moieties denoted by K; or
$D_4$ is OH and each of $D_1$-$D_3$, $D_5$-$D_6$ is independently selected from the group of moieties denoted by K; or
$D_5$ is OH and each of $D_1$-$D_4$, $D_6$ is independently selected from the group of moieties denoted by K; or
$D_6$ is OH and each of $D_1$-$D_5$ is independently selected from the group of moieties denoted by K; or
$D_2$ and $D_3$ are OH and each of $D_1$, $D_4$-$D_6$ is independently selected from the group of moieties denoted by K; or
$D_2$ and $D_4$ are OH and each of $D_1$, $D_3$, $D_5$-$D_6$ is independently selected from the group of moieties denoted by K; or D, and $D_5$ are OH and each of $D_1$, $D_3$-$D_4$, $D_6$ is independently selected from the group of moieties denoted by K; or
D, and $D_6$ are OH and each of $D_1$, $D_3$-$D_5$ is independently selected from the group of moieties denoted by K; or
$D_3$ and $D_5$ are OH and each of $D_1$-$D_2$$D_4$, $D_6$ is independently selected from the group of moieties denoted by K; or
$D_4$ and $D_6$ are OH and each of $D_1$-$D_3$, $D_5$ is independently selected from the group of moieties denoted by K; or
$D_2$ $D_3$ and $D_5$ are OH, and $D_1$, $D_4$, $D_6$ is independently selected from the group of moieties denoted by K; or
$D_2$, $D_4$ and $D_6$ are OH, and $D_1$, $D_3$, $D_5$ is independently selected from the group of moieties denoted by K;

and the second radiolabeled tracer comprises a compound selected from the group consisting of fused ring compounds having the formula (5)

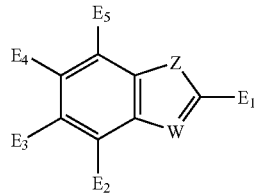

where Z is O, S, N—$R^1$ (wherein $R^1$ is H, alkyl, aryl, [$^{11}$C]methyl, [$^{18}$F]fluoroalkyl, [$^{18}$F]fluoroaryl, [$^{123}$I]iodoalkyl, [$^{123}$I]iodoaryl, [$^{124}$I]iodoalkyl, [$^{124}$I]iodoaryl,] [$^{125}$I]iodoalkyl, or [$^{125}$I]iodoaryl), $CH_2$, or CH=CH; and W is N or CH; and wherein
E2 is OH and each of E1, $E_3$-$E_5$ is independently selected from the group of moieties denoted by K; or
$E_3$ is OH and each of E1-E2, $E_4$-$E_5$ is independently selected from the group of moieties denoted by K; or
$E_4$ is OH and each of E1-$E_3$, $E_5$ is independently selected from the group of moieties denoted by K; or
$E_5$ is OH and each of E1-$E_4$ is independently selected from the group of moieties denoted by K; or
E2 and $E_4$ are OH and each of E1-$E_4$ is independently selected from the group of moieties denoted by K; or
$E_3$ and $E_5$ are OH and each of E1, E2, $E_4$, is independently selected from the group of moieties denoted by K;
and wherein in each case at least one of E1-$E_5$ or Z is or contains a radioisotope;
($e^1$) structurally related fused ring compounds in which E1 is a substituted aryl group, said compounds having the formula 5a:

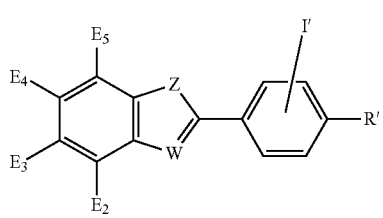

where Z is O, S, N—R(wherein $R_1$ is H, alkyl, aryl, [$^{11}$C]methyl, [$^{18}$F]fluoroalkyl, [$^{18}$F]fluoroaryl, [$^{123}$I]iodoalkyl, [$^{123}$I]iodoaryl, [$^{124}$I]iodoalkyl, [$^{124}$I]iodoaryl,] [$^{125}$I]iodoalkyl, or [$^{125}$I]iodoaryl), $CH_2$, or CH=CH; W is N or CH; and $I^1$ is H, alkyl, aryl, [$^{11}$C]methyl, $^{18}$F, [$^{18}$F]fluoroalkyl, [$^{18}$F]fluoroaryl, $^{123}$I, [$^{123}$I]iodoalkyl, [$^{123}$I]iodoaryl, [$^{124}$I]iodoalkyl, [$^{124}$I]iodoaryl,]$^{125}$I, [$^{125}$I]iodoalkyl, or [$^{125}$I]iodoaryl);
and wherein E2 is OH and each of $E_3$-$E_5$ is independently selected from the group of moieties denoted by K; or
$E_3$ is OH and each of E2, $E_4$-$E_5$ is independently selected from the group of moieties denoted by K; or $E_4$ is OH and each of E2-$E_3$, $E_5$ is independently selected from the group of moieties denoted by K; or
$E_5$ is OH and each of E2-$E_4$ is independently selected from the group of moieties denoted by K; or
E2 and $E_4$ are OH and each of $E_3$, $E_5$ is independently selected from the group of moieties denoted by K; or $E_3$ and $E_5$ are OH and each of E, $E_4$ is independently selected from the group of moieties denoted by K;

wherein in each case at least one of E1-$E_5$, $1^1$, or Z is or contains a radioisotope; and wherein $R^1$ is selected from the group consisting of H, NH—$CH_3$, $N(CH_3)_2$ $NH_2$, $OCH_3$, NH—CO—CH, F, I, CN, $NO_2$, $SO_2$-$CH_3$, and radiolabeled isotopes thereof; (f) imidazopyridines having the formula (6):

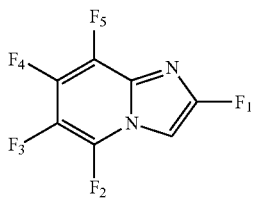

6 where $F_1$-$F_5$ are the same as E1-$E_5$, and wherein at least one of $F_1$-$F_5$ is or contains a radioisotope; and (g) stilbenes having the formula (7):

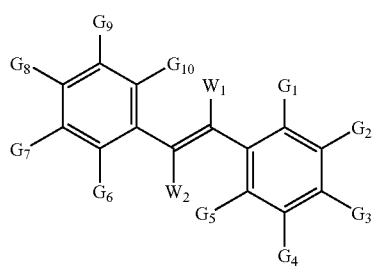

7 where $W_1$ and $W_2$ are, independently, alkyl, aryl, or OH; and wherein $G_3$ is OH and each of $G_1$-$G_2$, $G_4$-do is independently selected from the group of moieties denoted by K; or $G_2$ and $G_4$ are OH and each of $G_1$, $G_3$, $G_5$-$G_{10}$ is independently selected from the group of moieties denoted by K; or $G_3$ and $G_8$ are OH and each of $G_1$-$G_3$, $G_4$-$G_7$, $G_9$-$G_{10}$ is independently selected from the group of moieties denoted by K; or $G_2$=$G_4$=$G_8$=OH and each of $G_1$, $G_3$, $G_5$-$G_7$, $G_9$-$G_{10}$ is independently selected from the group of moieties denoted by K; and wherein in each case at least one of $G_1$-$G_{10}$ is or contains a radioisotope;

wherein in each case (a)-(g) K is selected from the group consisting of H; alkyl; aryl; $^{18}F$; [$^{18}F$]fluoroalkyl; [$^{18}F$]fluoroaryl; $^{123}I$; [$^{123}I$]iodoalkyl; [$^{123}I$]iodoaryl; $^{124}I$; [$^{124}I$]iodoalkyl; [$^{124}I$]iodoaryl; $^{125}I$; [$^{125}I$]iodoalkyl; [$^{125}I$]iodoaryl; —$OR^1$, —$SR^1$, or —$NR^1R^2$ (where $R^1$ and $R^2$ are independently H, alkyl, aryl, [$^{11}C$]methyl, [$^{18}F$]fluoroalkyl; [$r^8F$] fluoroaryl [$^{123}I$]iodoalkyl; [$^{123}I$]iodoaryl; [$^{124}I$]iodoalkyl; [$^{124}I$]iodoaryl; [$^{125}I$]iodoalkyl; or [$^{125}I$]iodoaryl); —$NO_2$; —CN; —S(=O)—$R^3$ or —S(=O)$_2$—$R^3$ (where $R^3$ is alkyl, aryl, [$^{11}C$]methyl, [$^{18}F$]fluoroalkyl, [$^{18}F$]fluoroaryl, [$^{123}I$]iodoalkyl, [$^{123}I$]iodoaryl, [$^{124}I$]iodoalkyl, [$^{124}I$]iodoaryl, [$^{125}I$] iodoalkyl, [$^{125}I$]iodoaryl), or —$OR^4$, —$NR^4R^5$, (wherein $R^4$ and $R^5$ are independently H, alkyl, aryl, [$^{11}C$]methyl, [$^{18}F$] fluoroalkyl, [$^{18}F$]fluoroaryl, [$^{123}i$]iodoalkyl, [$^{123}I$]iodoaryl, [$^{124}I$]iodoalkyl, [$^{124}I$]iodoaryl, [$^{125}I$]iodoalkyl, or [$^{125}I$]iodoaryl)); and —OC(=O)—$R^6$, —SC(=O)—$R^6$, or —NH—C(=O)—$R^6$ (where $R^6$ is alkyl, aryl, [$^{11}C$]methyl, [$^{18}F$]fluoroalkyl, [$^{18}F$]fluoroaryl, [$^{123}I$]iodoalkyl, [$^{123}I$]iodoaryl, [$^{124}I$] iodoalkyl, [$^{124}I$]iodoaryl, [$^{125}I$]iodoalkyl, or [$^{125}I$]iodoaryl).

21. A method as recited in claim 20, wherein the first radiolabeled tracer comprises a compound selected from formulae 5, 5a, 6, and 7, and the second radiolabeled tracer comprises a compound selected from formulae 1, 2, 3, and 4.

22. A method as recited in claim 16, wherein the first radiolabeled tracer is PIB and the second radiolabeled tracer is an [$^{18}F$]fluoronitrophenol.

23. A radiolabeled tracer for sulfotransferase, comprising at least one compound selected from the group consisting of (a) phenols having the formula (1)

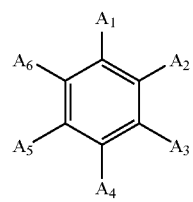

1 where $A_1$ is OH and each of $A_2$-$A_6$ is independently selected from the group of moieties denoted by "K" (defined below), provided that at least one of $A_2$-$A_6$ is or contains a radioisotope; or $A_1$ and $A_3$ are both OH and each of $A_2$, $A_4$-$A_6$ is independently selected from the group of moieties denoted by K, provided that at least one of $A_2$, $A_4$-$A_6$ is or contains a radioisotope;

(b) naphthols having the formula (2)

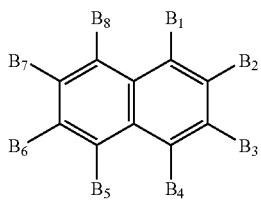

2 where $B_1$ is OH and each of $B_2$-$B_8$ is independently selected from the group of moieties denoted by K, provided that at least one of $B_2$-$B_8$ is or contains a radioisotope; or $B_2$ is OH and each of $B_1$, $B_3$-$B_8$ is independently selected from the group of moieties denoted by K, provided that at least one of $B_1$, $B_3$-$B_8$ is or contains a radioisotope; or $B_1$ and $B_3$ are each OH and each of $B_2$, $B_4$-$B_8$ is independently selected from the group of moieties denoted by K, provided that at least one of $B_4$-$B_8$ is or contains a radioisotope;

(c) coumarins having the formula (3)

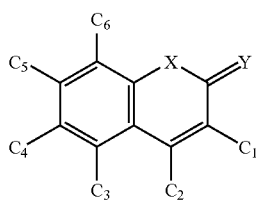

3 where X and Y are, independently, O, S, or N—R' (wherein $R_1$ is H, alkyl, aryl, [$^{11}C$]methyl, [$^{18}F$]fluoroalkyl, [$^{18}F$]fluoroaryl, [$^{123}I$]iodoalkyl, [$^{123}I$]iodoaryl, [$^{124}I$]iodoalkyl, [$^{124}I$]iodoaryl,] [$^{125}I$]iodoalkyl, or [$^{125}I$]iodoaryl); and wherein $C_3$ is OH and each of $C_1$-$C_2$, $C_4$-$C_6$ is independently selected from the group of moieties denoted by K; or
$C_4$ is OH and each of $C_1$-$C_3$, $C_5$-$C_6$ is independently selected from the group of moieties denoted by K; or
$C_5$ is OH and each of $C_1$-$C_4$, $C_6$ is independently selected from the group of moieties denoted by K; or
$C_6$ is OH and each of $C_1$-$C_5$ is independently selected from the group of moieties denoted by K; or
$C_2$ and $C_3$=OH and each of $C_1$, $C_4$-$C_6$ is independently selected from the group of moieties denoted by K; or
$C_2$ and $C_4$=OH and each of $C_1$, $C_3$, $C_5$-$C_6$ is independently selected from the group of moieties denoted by K; or
$C_2$ and $C_5$=OH and each of $C_1$, $C_3$-$C_4$, $C_6$ is independently selected from the group of moieties denoted by K; or
$C_2$ and $C_6$=OH and each of $C_1$, $C_3$-$C_5$ is independently selected from the group of moieties denoted by K; or
$C_3$ and $C_5$=OH and each of $C_1$-$C_2$, $C_4$, $C_6$ is independently selected from the group of moieties denoted by K; or
$C_4$ and $C_6$=OH and each of $C_1$-$C_3$, $C_5$ is independently selected from the group of moieties denoted by K; or
$C_2$=$C_3$=$C_5$=OH and each of $C_1$, $C_4$, $C_6$ is independently selected from the group of moieties denoted by K; or
$C_2$, $C_4$ and $C_6$=OH and each of $C_1$, $C_3$, $C_5$ is independently selected from the group of moieties denoted by K;
wherein in each case at least one of $C_1$-$C_6$, X, or Y is or contains a radioisotope;
(d) flavones having the formula (4)

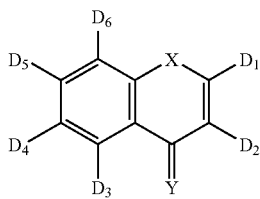

where X and Y are, independently, O, S, or N—$R^1$ (wherein $R_1$ is H, alkyl, aryl, [$^{11}$C]methyl, [$^{18}$F]fluoroalkyl, [$^{18}$F]fluoroaryl, [$^{123}$I]iodoalkyl, [$^{123}$I]iodoaryl, [$^{124}$I]iodoalkyl, [$^{124}$I]iodoaryl,] [$^{125}$I]iodoalkyl, or [$^{125}$I]iodoaryl); and wherein
$D_3$ is OH and each of $D_1$-$D_2$, $D_4$-$D_6$ is independently selected from the group of moieties denoted by K; or
$D_4$ is OH and each of $D_1$-$D_3$, $D_5$-$D_6$ is independently selected from the group of moieties denoted by K; or
$D_5$ is OH and each of $D_1$-$D_4$, $D_6$ is independently selected from the group of moieties denoted by K; or
$D_6$ is OH and each of $D_1$-$D_5$ is independently selected from the group of moieties denoted by K; or
$D_2$ and $D_3$ are OH and each of $D_1$, $D_4$-$D_6$ is independently selected from the group of moieties denoted by K; or
$D_2$ and $D_4$ are OH and each of $D_1$, $D_3$, $D_5$-$D_6$ is independently selected from the group of moieties denoted by K; or
$D_2$ and $D_5$ are OH and each of $D_1$, $D_3$-$D_4$, $D_6$ is independently selected from the group of moieties denoted by K; or
$D_2$ and $D_6$ are OH and each of $D_1$, $D_3$-$D_5$ is independently selected from the group of moieties denoted by K; or
$D_3$ and $D_5$ are OH and each of $D_1$-$D_2$, $D_4$, $D_6$ is independently selected from the group of moieties denoted by K; or
$D_4$ and $D_6$ are OH and each of $D_1$-$D_3$, $D_5$ is independently selected from the group of moieties denoted by K; or
$D_2$, $D_3$ and $D_5$ are OH, and $D_1$, $D_4$, $D_6$ is independently selected from the group of moieties denoted by K; or
$D_2$, $D_4$ and $D_6$ are OH, and $D_1$, $D_3$, $D_5$ is independently selected from the group of moieties denoted by K;
wherein in each case at least one of $D_1$-$D_6$, X, or Y is or contains a radioisotope;
and wherein K is selected from the group consisting of H; alkyl; aryl; $^{18}$F; [$^{18}$F]fluoroalkyl; [$^{18}$F]fluoro aryl; $^{123}$I; [$^{123}$I]iodoalkyl; [$^{123}$I]iodoaryl; $^{124}$I; [$^{124}$I]iodoalkyl; [$^{124}$I]iodoaryl; $^{125}$I; [$^{125}$I]iodoalkyl; [$^{125}$I]iodoaryl; —$OR^1$, —$SR^1$, or —$NR^1R^2$ (where $R^1$ and $R^2$ are independently H, alkyl, aryl, [α]methyl; [$^{18}$F]fluoroalkyl; [$^{18}$F]fluoroaryl; [$^{123}$I]iodoalkyl; [$^{123}$I]iodoaryl; [$^{124}$I]iodoalkyl; [$^{124}$I]iodoaryl; [$^{125}$I]iodoalkyl; or [$^{125}$I]iodoaryl); —$NO_2$; —CN; —S(=O)—$R^3$ or —S(=O)$_2$—$R^3$ (where $R^3$ is alkyl, aryl, [$^{11}$C]methyl, [$^{18}$F]fluoroalkyl, [$^{18}$F]fluoroaryl, [$^{123}$I]iodoalkyl, [$^{123}$I]iodoaryl, [$^{124}$I]iodoalkyl, [$^{124}$I]iodoaryl, [$^{125}$I]iodoalkyl, [$^{125}$I]iodoaryl), or —$OR^4$, —$NR^4R^5$, (wherein $R^4$ and $R^5$ are independently H, alkyl, aryl, [$^{11}$C]methyl, [$^{18}$F]fluoroalkyl, [$^{18}$F]fluoroaryl, [$^{123}$I]iodoalkyl, [$^{123}$I]iodoaryl, [$^{124}$I]iodoalkyl, [$^{124}$I]iodoaryl, [$^{125}$I]iodoalkyl, or [$^{125}$I]iodoaryl)); and —OC(=O)—$R^6$, —SC(=O)—$R^6$, or —NH—C(=O)—$R^6$ (where $R^6$ is alkyl, aryl, [$^{11}$C]methyl, [$^1$F]fluoroalkyl, [$^{18}$F]fluoroaryl, [$^{123}$I]iodoalkyl, [$^{123}$I]iodoaryl, [$^{124}$I]iodoalkyl, [$^{124}$I]iodoaryl, [$^{125}$I]iodoalkyl, or [$^{125}$I]iodoaryl).

* * * * *

UNITED STATES PATENT AND TRADEMARK OFFICE
CERTIFICATE OF CORRECTION

PATENT NO. : 8,372,380 B2
APPLICATION NO. : 12/594197
DATED : February 12, 2013
INVENTOR(S) : Jorge R. Barrio et al.

It is certified that error appears in the above-identified patent and that said Letters Patent is hereby corrected as shown below:

In the Claims

Column 27, Claim 1, line 64    Delete "[$^{124}$]iodoalkyl,"
                                Insert -- [$^{124}$I]iodoalkyl, --

Column 29, Claim 1, line 16    Delete "I''"
                                Insert -- I' --

Column 31, Claim 7, line 64    Delete "[$^{124}$I]iiodoalkyl"
                                Insert -- [$^{124}$I]iodoalkyl --

Column 31, Claim 7, lines 64-65    Delete "[$^{124}$]iodoaryl"
                                    Insert -- [$^{124}$I]iodoaryl --

Column 33, Claim 7, line 50    Delete "[[$^{124}$]iodoalkyl,"
                                Insert -- [$^{124}$I]iodoalkyl, --

Column 33, Claim 7, line 50    Delete "[[$^{124}$]iodoaryl"
                                Insert -- [$^{124}$I]iodoaryl --

Column 33, Claim 7, line 54    Delete "[$^{124}$]iodoalkyl,"
                                Insert -- [$^{124}$I]iodoalkyl, --

Signed and Sealed this
Second Day of December, 2014

Michelle K. Lee
*Deputy Director of the United States Patent and Trademark Office*

CERTIFICATE OF CORRECTION (continued)

U.S. Pat. No. 8,372,380 B2

In the Claims (continued)

| | |
|---|---|
| Column 33, Claim 7, line 54 | Delete "[$^{124}$]iodoaryl" |
| | Insert -- [$^{124}$I]iodoaryl -- |
| Column 35, Claim 18, line 61 | Delete "16" |
| | Insert -- 17 -- |
| Column 38, Claim 20, line 56 | After "iodoaryl," |
| | Insert -- $^{124}$I, -- |
| Column 42, Claim 23, line 30 | Delete "[α]methyl," |
| | Insert -- [$^{11}$C]methyl, -- |